United States Patent
Moudy

(10) Patent No.: US 10,857,331 B2
(45) Date of Patent: Dec. 8, 2020

(54) SECURE LINE HOLDER

(71) Applicant: Creative Medical Devices LLC, Phoenix, AZ (US)

(72) Inventor: Joanne Moudy, Phoenix, AZ (US)

(73) Assignee: CREATIVE MEDICAL DEVICES LLC, Phoenix, AZ (US)

( * ) Notice: Subject to any disclaimer, the term of this patent is extended or adjusted under 35 U.S.C. 154(b) by 0 days.

(21) Appl. No.: 16/779,483

(22) Filed: Jan. 31, 2020

(65) Prior Publication Data

US 2020/0306117 A1    Oct. 1, 2020

Related U.S. Application Data

(60) Provisional application No. 62/826,624, filed on Mar. 29, 2019.

(51) Int. Cl.
*A61M 25/02* (2006.01)
*A61G 13/10* (2006.01)

(52) U.S. Cl.
CPC .......... *A61M 25/02* (2013.01); *A61G 13/101* (2013.01); *A61G 13/107* (2013.01); *A61M 2025/028* (2013.01); *A61M 2209/082* (2013.01)

(58) Field of Classification Search
None
See application file for complete search history.

(56) References Cited

U.S. PATENT DOCUMENTS

| | | | |
|---|---|---|---|
| 2,449,882 A | 9/1948 | Daniels | |
| 3,203,655 A | * 8/1965 | Mejlso | F16L 3/2235 248/68.1 |
| 3,894,706 A | * 7/1975 | Mizusawa | F16L 3/1025 248/68.1 |
| 4,224,937 A | 9/1980 | Gordon | |
| 4,250,880 A | 2/1981 | Gordon | |
| 4,397,647 A | 8/1983 | Gordon | |
| D290,041 S | 5/1987 | Scott | |
| 5,084,026 A | 1/1992 | Shapiro | |
| 5,316,246 A | 5/1994 | Scott et al. | |
| 5,323,992 A | 6/1994 | Sifers et al. | |
| 5,336,179 A | * 8/1994 | Ryan | A61M 5/1418 128/DIG. 26 |
| 5,427,338 A | 6/1995 | Garrett et al. | |
| D378,408 S | 3/1997 | Pyeatt et al. | |
| 5,876,371 A | 3/1999 | Yokoyama et al. | |

(Continued)

FOREIGN PATENT DOCUMENTS

WO    2017147071 A1    8/2017

*Primary Examiner* — David R Hare
*Assistant Examiner* — Adam C Ortiz
(74) *Attorney, Agent, or Firm* — John J. Barnert, Esq.; Lowe Graham Jones PLLC

(57) ABSTRACT

Embodiments are directed toward a medical line holder system. The system preferably includes a tray and a secure line holder. The tray preferably has a holder receptacle. The tray preferably couples to a head of a surgery bed. The holder receptacle preferably receives and separably secures the secure line holder. The secure line holder preferably securely holds multiple medical lines both while being secured in the receptacle and while being separated from the tray. The secure line holder preferably separably couples to a bed rail of a hospital transportation bed or a hospital recovery bed after being separated from the tray.

12 Claims, 21 Drawing Sheets

(56) References Cited

U.S. PATENT DOCUMENTS

| | | | |
|---|---|---|---|
| 6,464,530 B1* | 10/2002 | Smith | H01R 13/5833 |
| | | | 439/449 |
| 7,457,506 B1 | 11/2008 | Osborne, II | |
| D657,869 S | 4/2012 | Mammen | |
| D715,427 S | 10/2014 | Jovet-Hug et al. | |
| 10,433,926 B2 | 10/2019 | Recanati et al. | |
| 2001/0045763 A1* | 11/2001 | Jacoway | A47C 3/16 |
| | | | 297/16.1 |
| 2001/0049504 A1* | 12/2001 | Gautsche | A61M 5/1418 |
| | | | 604/174 |
| 2005/0103949 A1 | 5/2005 | Ross et al. | |
| 2006/0113432 A1 | 6/2006 | Driskell | |
| 2009/0019678 A1 | 1/2009 | Taylor | |
| 2011/0118670 A1 | 5/2011 | Kay et al. | |
| 2011/0248125 A1 | 10/2011 | D'Andria | |
| 2014/0252177 A1 | 9/2014 | Vera | |
| 2014/0306070 A1 | 10/2014 | Hartsock et al. | |
| 2015/0144746 A1 | 5/2015 | Stewart | |
| 2016/0114103 A1 | 4/2016 | Burke | |
| 2017/0246371 A1 | 8/2017 | Biewer et al. | |
| 2019/0022303 A1 | 1/2019 | Headlee et al. | |

\* cited by examiner

SECURE LINE HOLDER

CROSS REFERENCE TO RELATED APPLICATIONS

This application claims the benefit of the filing date of U.S. Provisional Application No. 62/826,624, filed 29 Mar. 2019, titled SECURE LINE HOLDER, the entirety of which is incorporated herein by reference.

FIELD OF THE INVENTION

The present invention relates to a secure line holder and, more particularly yet not exclusively, a secure line holder for securing and managing medical lines, such as catheters.

BACKGROUND OF THE INVENTION

When a patient is admitted to a hospital, the patient typically lays in a bed, and many lines typically extend to the patient's body from medical equipment (for example, monitors, pumps, drip bags, drainage bags, or other equipment). The lines typically drape across the bed (for example, the upper bed) and over the patient's body (for example, the patient's chest). The lines often include one or more catheters (for example, catheters feeding peripheral venous catheters, catheters feeding central venous catheters, catheters feeding ports implanted in patients, urinary catheters, or other catheters) or wires (for example, stimulation wires, monitor wires, or other wires). As more lines are run between the patient and the equipment or after the patient moves, medical personnel (for example, nurses, physician assistants, physicians, or other medical personnel) experience increasing difficulty in identifying which line is associated with which procedure, treatment, or equipment. As more lines are run between the patient and the equipment or after the patient moves, the lines become increasingly tangled, thereby further increasing the difficulty in distinguishing between the lines. The patient is also susceptible to becoming entangled in the lines. The difficulties presented by the quantity of lines or their entanglement are especially troublesome in critical care settings where higher quantities of lines are involved and treatment often needs to be swiftly changed or modified.

A practical solution to distinguishing between lines is color coding or labeling of the lines themselves. However, this approach has proven insufficient. For color coded lines, medical practitioners must first look to a line source to identify a color associated with a line termination point of interest (for example, sensor attached to the patient's body, implanted port, catheter lumen, or medical equipment) and then follow a line of the identified color along its entire path to untangle it. For labeled lines, medical practitioners must first either do the same as with color coded lines or search along the longitudinal axis of each line until the appropriate label is found and then follow a corresponding line having the appropriate label along its entire path to untangle it.

These problems are further complicated when the patient undergoes surgery in a surgery bed and is subsequently transported in a transport bed and transitioned to a recovery or extended-stay bed. Transitioning the patient between each of these beds is challenging with so many lines connected to the patient, and organizing the lines during or after these transitions is time consuming. Moreover, the lines take different paths during surgery than during transportation and subsequent recovery. During surgery, the lines extend from equipment over the head of the bed and to the patient. In contrast, during transportation and subsequent recovery or extended stays, the lines can extend from equipment over the side of the bed or over and behind the head of the bed and to the patient. Accordingly, manipulating the organization of the lines to conform to the status of the patient further increases the amount of time consumed by organizing the lines and transitioning the patient.

U.S. Pat. No. 5,323,992 issued to Sifers et al., U.S. Pat. No. 5,336,179 issued to Ryan, U.S. Pat. No. 5,427,338 issued to Garrett et al., U.S. Pre-Grant Publication No. 2006/0113432 issued to Driskell, U.S. Pre-Grant Publication No. 2011/0248125 issued to D'Andria, U.S. Pat. No. D657,869 issued to Mammen, U.S. Pre-Grant Publication No. 2014/0252177 issued to Vera, U.S. Pre-Grant Publication No. 2016/0114103 issued to Burke, U.S. Pre-Grant Publication No. 2019/0022303 issued to Headlee et al., and U.S. Pat. No. 10,433,926 issued to Recanati et al. teach line holders for patients in hospital beds. Line holders that are configured to couple to machines include those taught by U.S. Pre-Grant Publication No. Biewer et al. Line holders that are configured to couple to patients' bodies include those taught by U.S. Pat. No. 4,397,647 issued to Gordon and U.S. Pat. No. 5,084,026 issued to Shapiro.

The known line holders such as those mentioned above, whether considered individually or in combination, teach only partial solutions to the issues surrounding securing lines. The known line holders make it challenging for medical personnel to quickly couple or decouple lines to or from the known line holders, especially in an emergency where the medical personnel are already thinking about the next step. The known line holders also fail to protect secured lines from snagging during transportation or other subsequent activities after surgery, such as snagging by the patient in the bed or medical personnel working on or around the patient. The known line holders also fail to (a) facilitate securing and organizing lines in a surgery bed in a manner that satisfies the requirements for surgery on the patient in the surgery bed and (b) also facilitate securing and organizing the lines in a transportation bed and optionally a recovery or extended-stay bed during transportation and other subsequent activities after surgery (for example, recovery or extended bed rest in hospital or at home) in manners that satisfy the separate and distinct requirements for those respective activities.

SUMMARY OF THE INVENTION

It is therefore an object of the present invention to provide systems for securing medical lines on hospital beds that facilitate securing and organizing the lines in both surgery beds and subsequent beds, such as transportation beds, recovery beds, or extended-stay beds.

It is also an object of the present invention to provide systems for securing medical lines on hospital beds that achieve the above object and that also provide improved efficiency for coupling or decoupling the lines to or from line holders.

It is another object of the present invention to provide systems for securing medical lines on hospital beds that achieve the above objects and that also protect secured lines from snagging during transportation of the patient or other activities subsequent to surgery.

The invention achieves the above objects, as well as other objects and advantages that will become apparent from the description that follows, by providing a medical line holder system. In some versions, the medical line holder system includes a tray and a secure line holder. The tray preferably has a holder receptacle. The tray is preferably configured to couple to a head of a surgery bed. The holder receptacle is preferably configured to receive and separably secure the secure line holder. The secure line holder is preferably configured to securely hold multiple medical lines both while being secured in the receptacle and while being separated from the tray. The secure line holder is preferably configured to separably couple to a bed rail of a hospital transportation bed or a hospital recovery bed after being separated from the tray.

In some versions, the tray has a longitudinal axis. The secure line holder preferably defines a plurality of line channels that are each configured to securely hold a respective one of the multiple medical lines. The secure line holder preferably has a first coupler and a second coupler disposed opposite the line channels from the first coupler. The first and second couplers of the secure line holder are preferably configured to separably couple to the tray.

In some versions, the secure line holder is disposed along the longitudinal axis of the tray while being secured in the receptacle. The secure line holder is preferably configured to orient the held medical lines with longitudinal axes of the held medical lines oriented transverse to the longitudinal axis of the tray while the secure line holder is secured in the receptacle and parallel to the bed rail while the secure line holder is coupled to the bed rail.

In some versions, the secure line holder defines a finger channel. The finger channel preferably extends along the longitudinal axis of the tray while the secure line holder is secured in the receptacle. The finger channel is preferably configured to receive an instrument between the secure line holder and a held line to facilitate removal of the line from the secure line holder.

In some versions, the receptacle of the tray has an elevated portion and a recessed portion. The secure line holder preferably has a rail coupler that couples the secure line holder to the bed rail. The elevated portion preferably supports the secure line coupler. The recessed portion of the receptacle preferably aligns with the rail coupler while the secure line holder is secured to the tray to facilitate storing the rail coupler between the secure line holder and the tray.

In some versions, the tray has a sidewall. The sidewall preferably extends along the longitudinal axis of the tray. The sidewall preferably has a high region and a low region sequentially distributed along the sidewall.

In some versions, the tray has holder fastener. The high region of the sidewall preferably aligns with the fastener relative to a position of the fastener along the longitudinal axis of the tray.

In some versions, the tray has a flange that extends away from the receptacle along the longitudinal axis of the tray.

The invention also achieves the above objects, as well as other objects and advantages that will become apparent from the description that follows, by providing a method of securing medical lines. The method preferably includes providing the medical line holder system. The tray is preferably coupled to the head of the surgery bed. The multiple medical lines are preferably secured to the secure line holder. After surgery of a patient, the secure line holder is preferably removed from the tray. The secure line holder is preferably coupled to the bed rail of the hospital transportation bed or the hospital recovery bed.

In some versions, the multiple medical lines are secured to the secure line holder while the secure line holder is coupled to the tray.

In some versions, the secure line holder is removed from the tray without removing the multiple medical lines from the secure line holder.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

Figure 1:
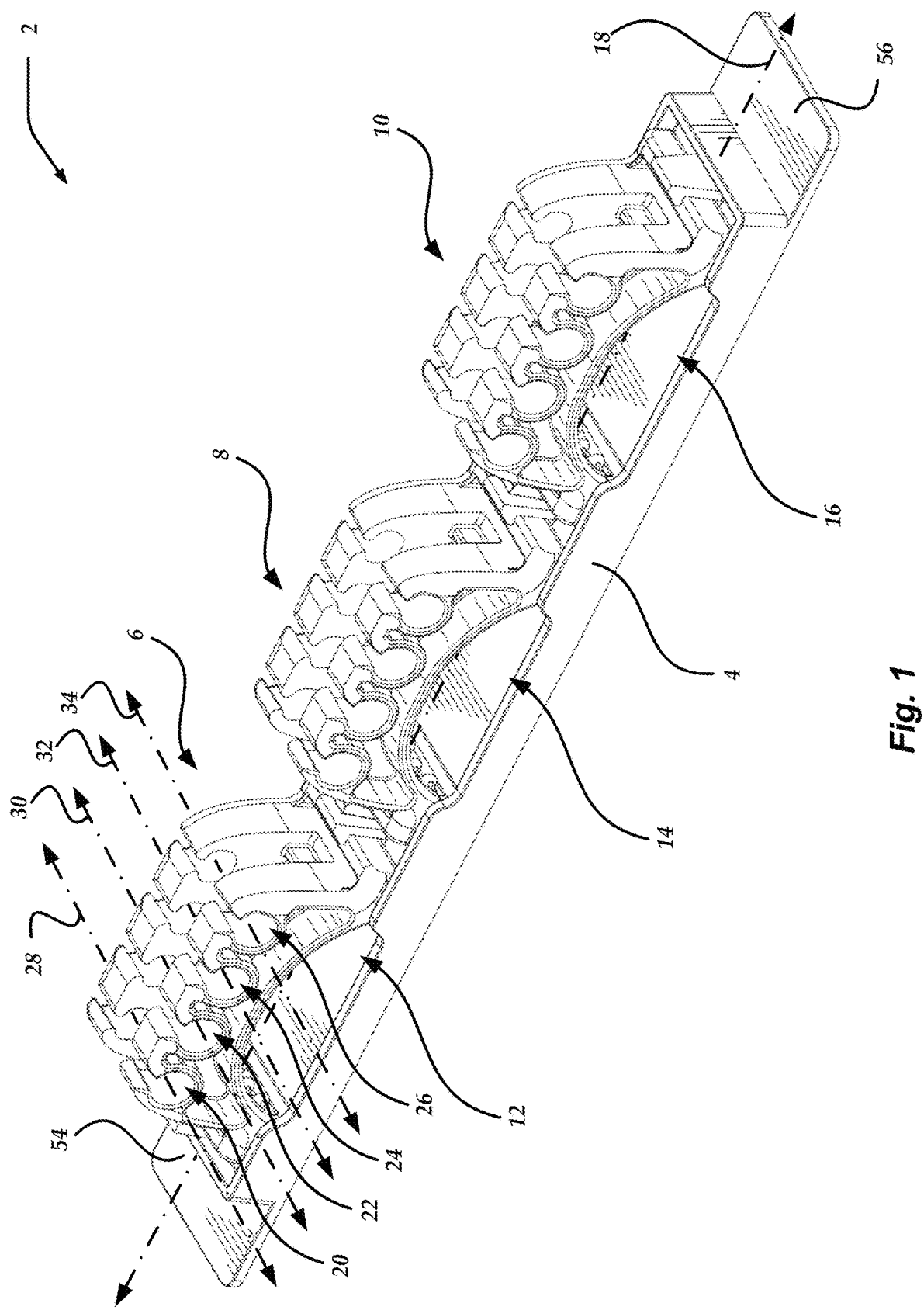
FIG. 1 is a perspective isometric view of a secure line holder system, including a tray and multiple secure line holders.
Figure 2:
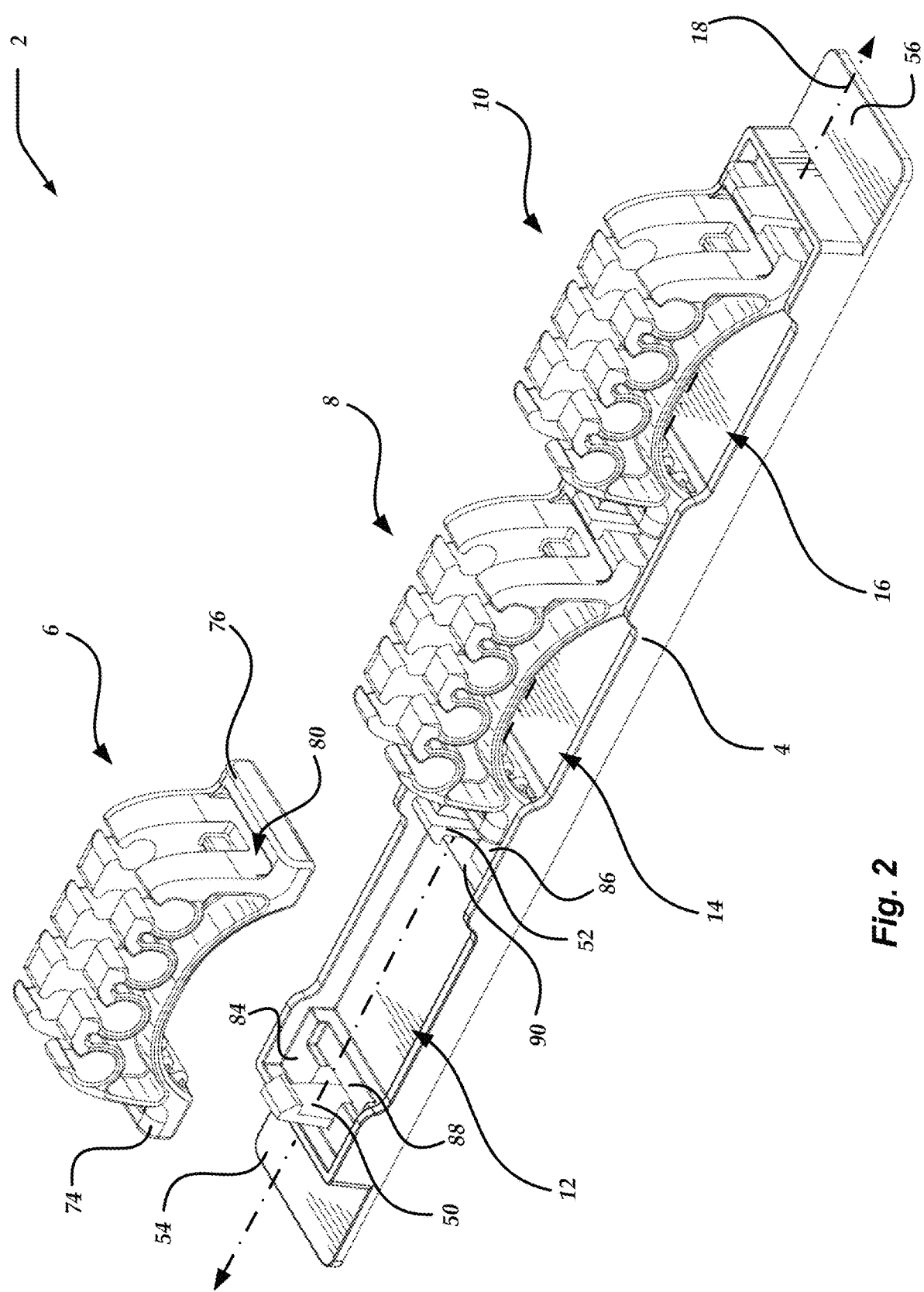
FIG. 2 is a perspective isometric view of the secure line holder system of FIG. 1, with one of the secure line holders separated from the tray.
Figure 3:
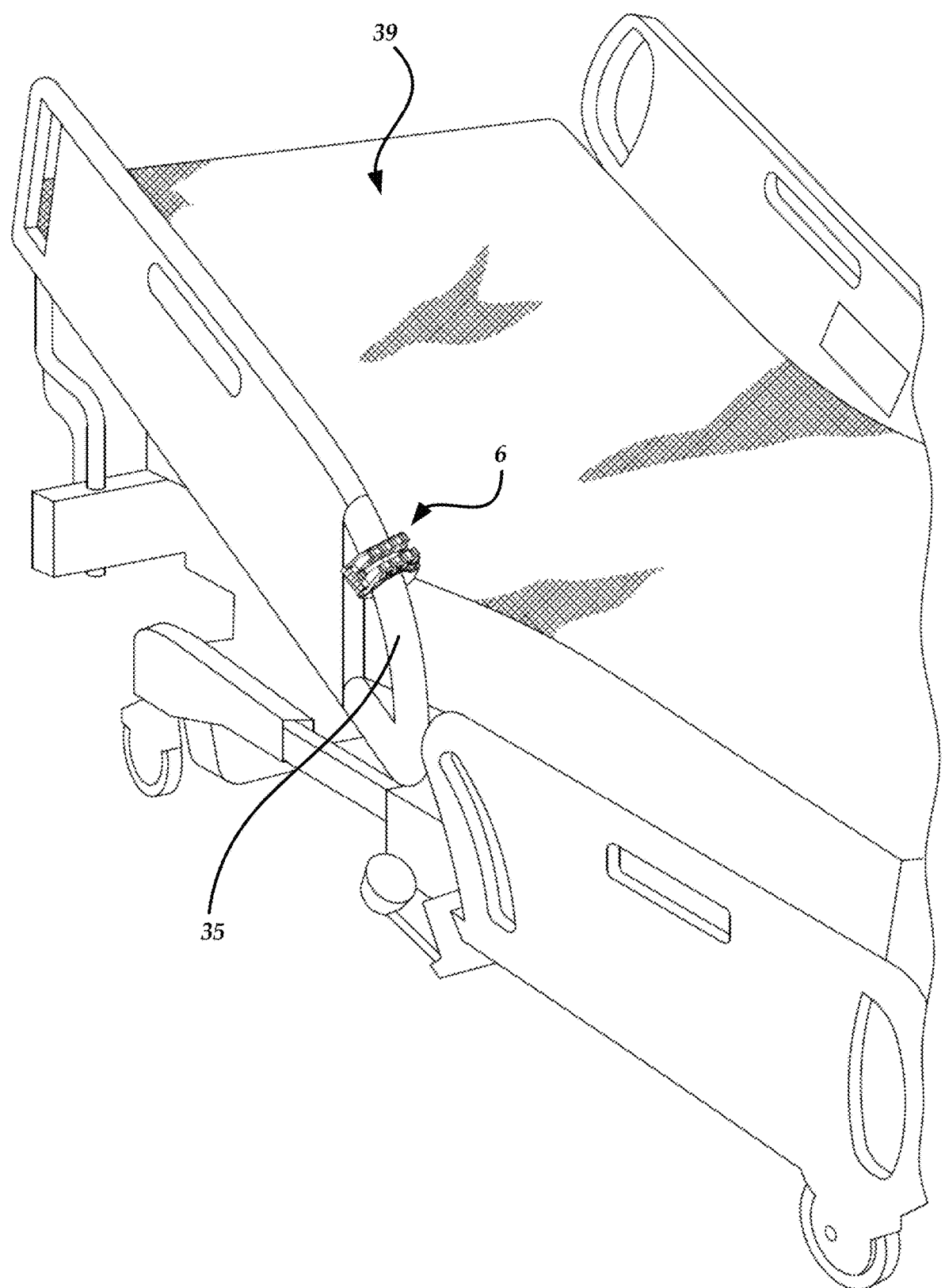
FIG. 3 is a perspective isometric view of the separated secure line holder of FIG. 2 coupled to a bed rail.
Figure 4:
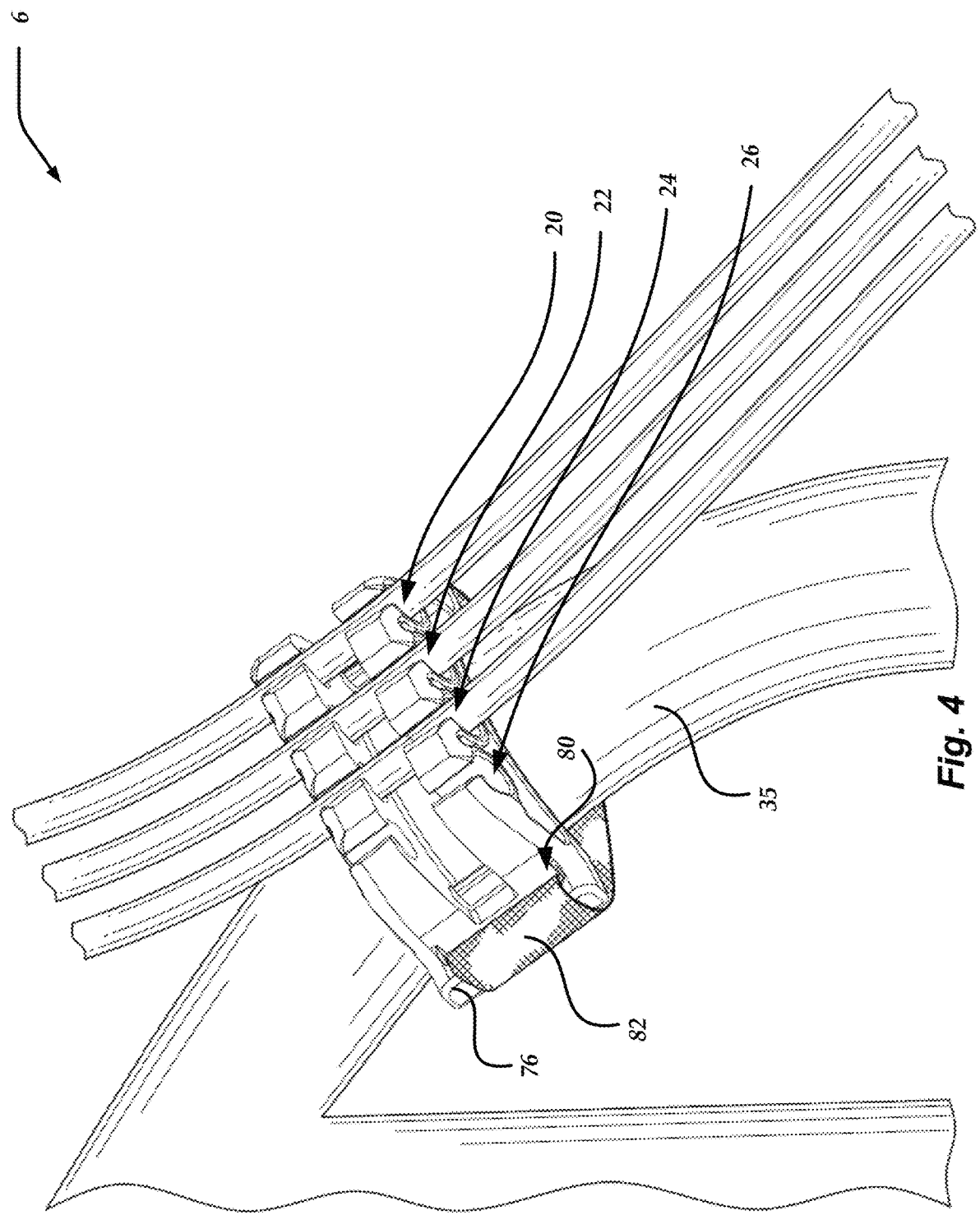
FIG. 4 is perspective isometric view of the secure line holder of FIG. 3 holding multiple lines.

FIGS. 1 and 2 show a preferred secure line holder system 2. The line holder system 2 preferably includes a tray 4 and one or more secure line holders, such as secure line holders 6-10. The tray 4 preferably defines a holder receptacle for each secure line holder in the system 2, such as receptacles 12-16, which are preferably distributed along the longitudinal axis 18 of the tray 4. The receptacles 12-16 are preferably configured (for example, sized and dimensioned) to receive and separably secure respective ones of the secure line holders 6-10. Each secure line holder preferably has multiple line channels, such as line channels 20-26, that are configured (for example, sized and dimensioned) to receive and secure respective medical lines, such as catheters or wires, that extend along the longitudinal axes of the corresponding line channels when secured therein, such as the longitudinal axes 28-34 of the line channels 20-26 (see FIG. 4). Each of the secure line holders 6-10 is preferably configured to couple to a bed rail (for example, bed rail 35 of a recovery bed 37 having a head 39, as shown in FIGS. 3 and 4) or another apparatus. Accordingly, the secure line holders 6-10 are preferably secured to the tray 4 as shown in FIG. 1 while the tray 4 is secured to the head of a surgery bed and lines are secured in the secure line holders 6-10, and, after surgery, one or more of the secure line holders 6-10 are separated from the tray 4 as shown in FIG. 2 and secured to a transportation bed and subsequently a recovery bed or other apparatus, as shown in FIGS. 3 and 4.

The receptacles 12-16 are configured (for example, sized, dimensioned, positioned, and oriented) to arrange (for example, orient) the respective secure line holders 6-10 that are secured to the tray 4 with the longitudinal axes of the line channels transverse to the longitudinal axis 18 of the tray 4, thereby facilitating arranging (for example, orienting) the lines secured in the secure line holders 6-10 that are secured to the tray 4 transverse to the longitudinal axis 18 of the tray 4. The secure line holders 6-10 are preferably configured to arrange the lines secured in the secure line holders 6-10 parallel to the bed rail when the secure line holders 6-10 are separated from the tray 4 and secured to the bed rail (see FIGS. 3 and 4).

Figure 6:
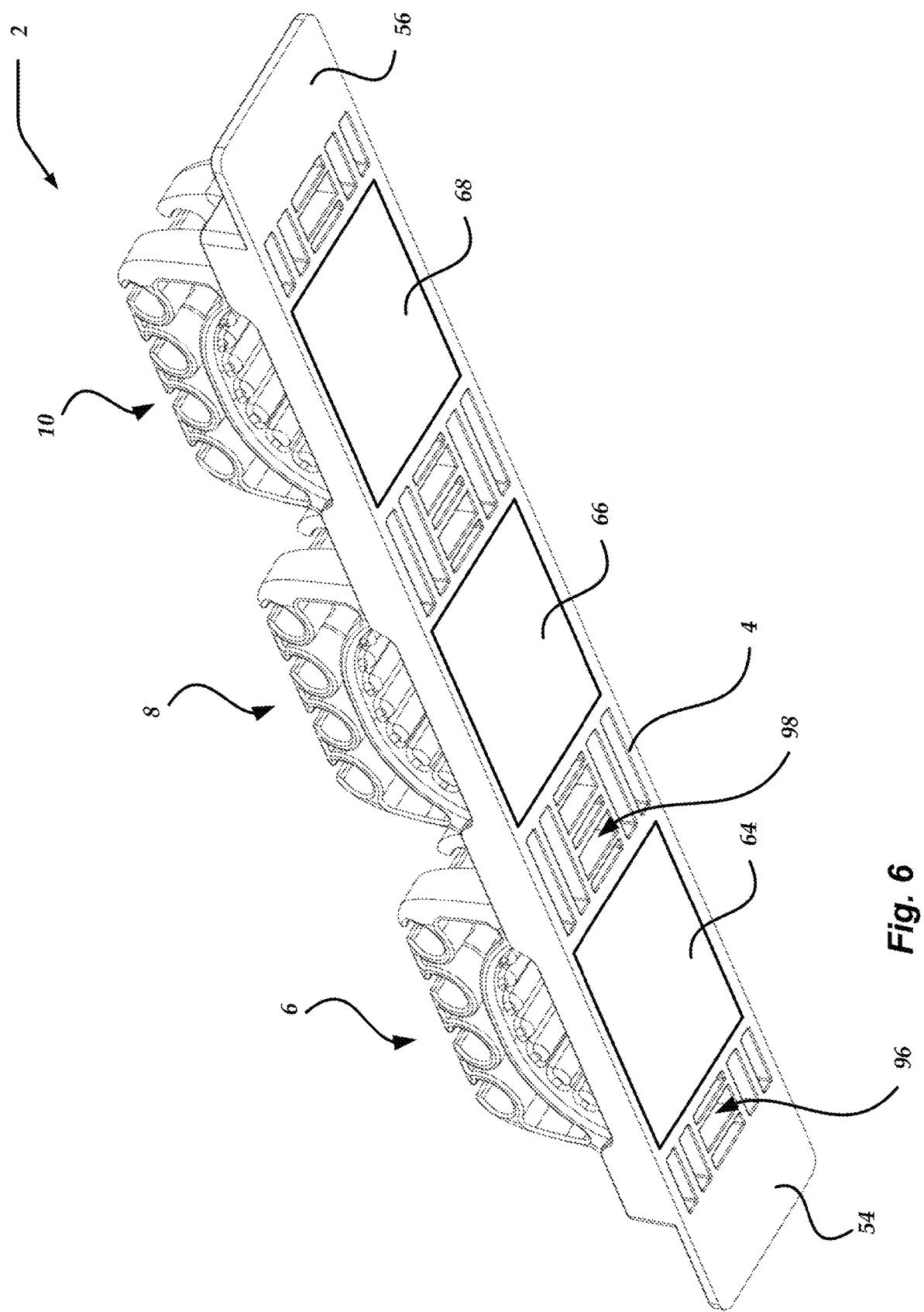
FIG. 6 is a perspective isometric underside view of the secure line holder system of FIG. 1.
Figure 12:
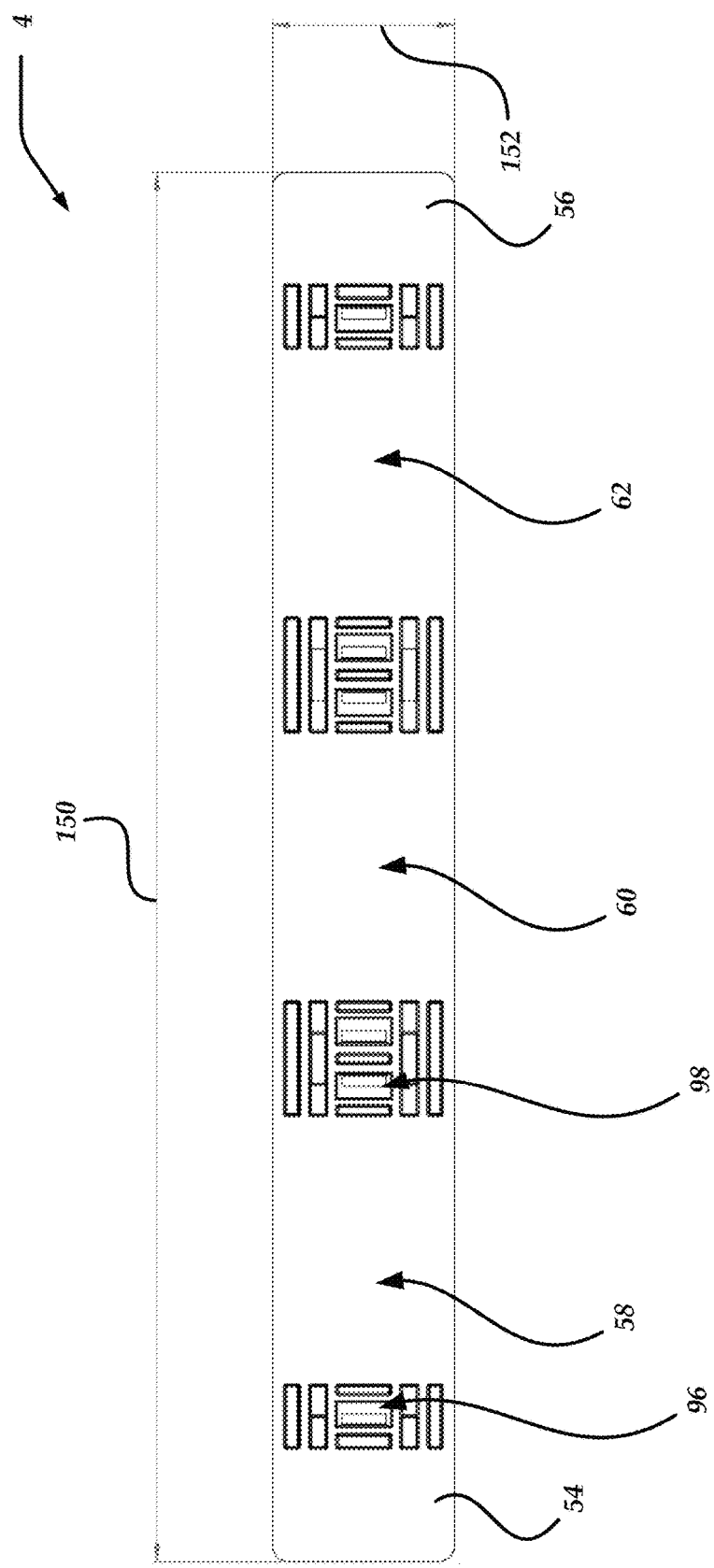
FIG. 12 is an isometric underside view of the tray of FIG. 1.
Figure 13:
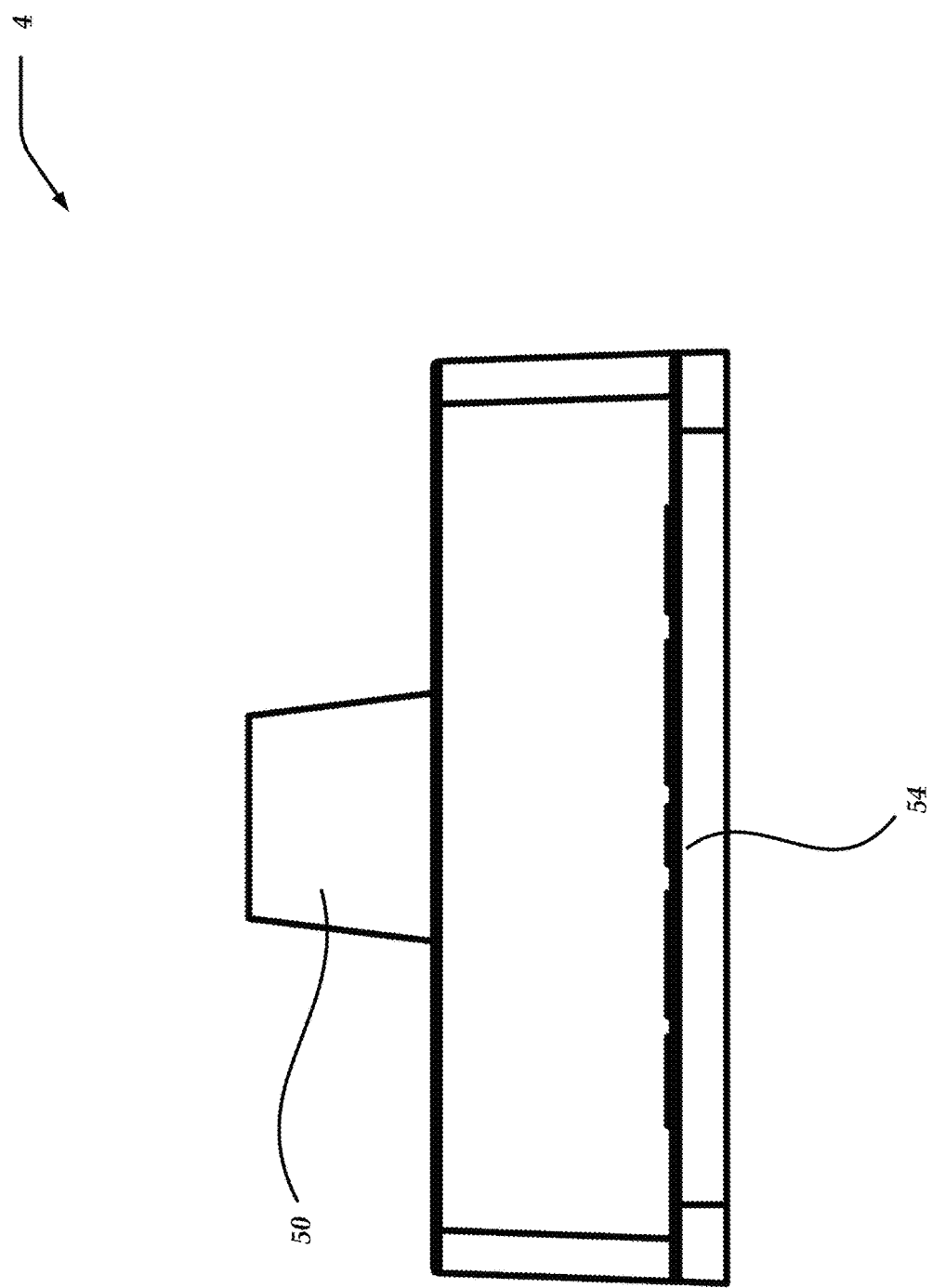
FIG. 13 is an isometric side elevational view of the tray of FIG. 1.

The bottom of the tray 4 preferably has one or more flat sections, such as flat sections 58-62 (see FIG. 12), that are configured to receive one or more bed fasteners, such as adhesive or double-sided tape 64-68 (see FIG. 6), to facilitate securing the tray 4 to the top surface of the head of the surgery bed (for example, the upward facing surface of a mattress or table on which the patient lies during surgery—see the head 39 of the recovery bed 37 as an example of a head of a bed). In some versions, the system 2 includes the one or more bed fasteners disposed on the one or more flat sections, and the medical personnel peels off a protective layer to expose a fastening surface, such as adhesive, before securing the tray 4 to the surgery bed. The tray 4 preferably has one or more couplers such as flanges, for example flanges 54 and 56 disposed opposite the one or more flat sections from each other, that provide grips for medical personnel to grasp to peel the tray off the surface of the surgery bed (see FIG. 1).

Figure 7:
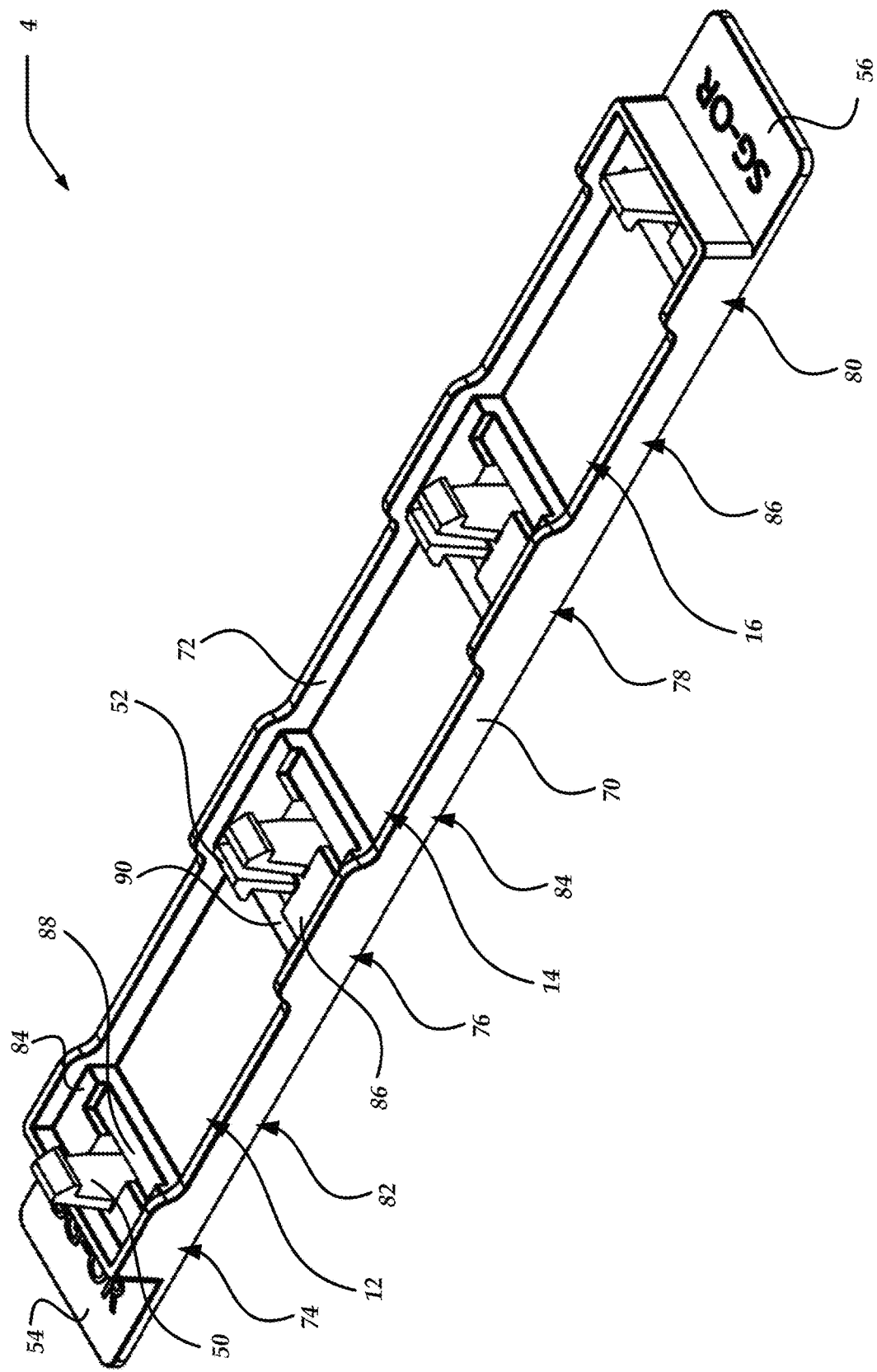
FIG. 7 is a perspective isometric view of the tray of FIG. 1.
Figure 10:
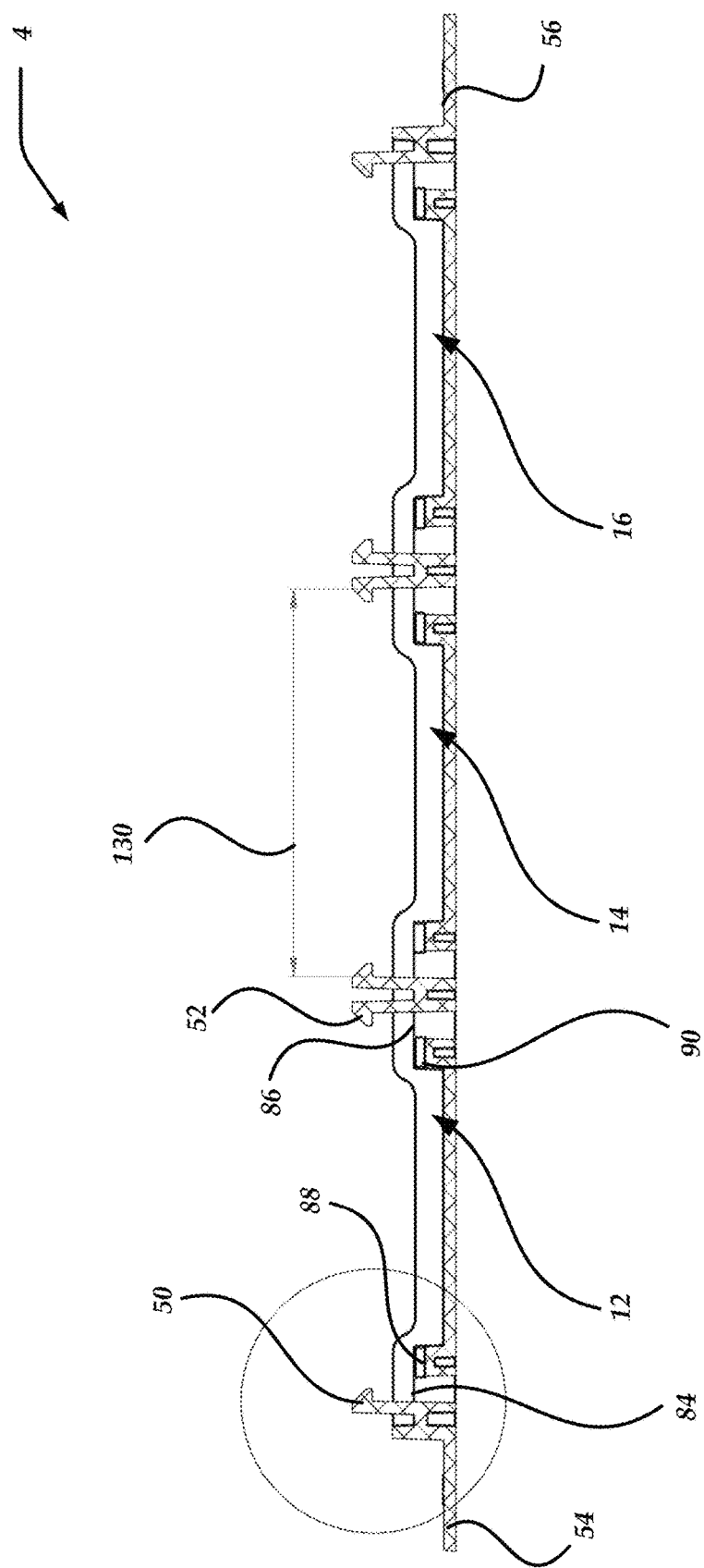
FIG. 10 is an isometric cross-sectional view of the tray of FIG. 1 taken along line 10-10 in FIG. 8.
Figure 17:
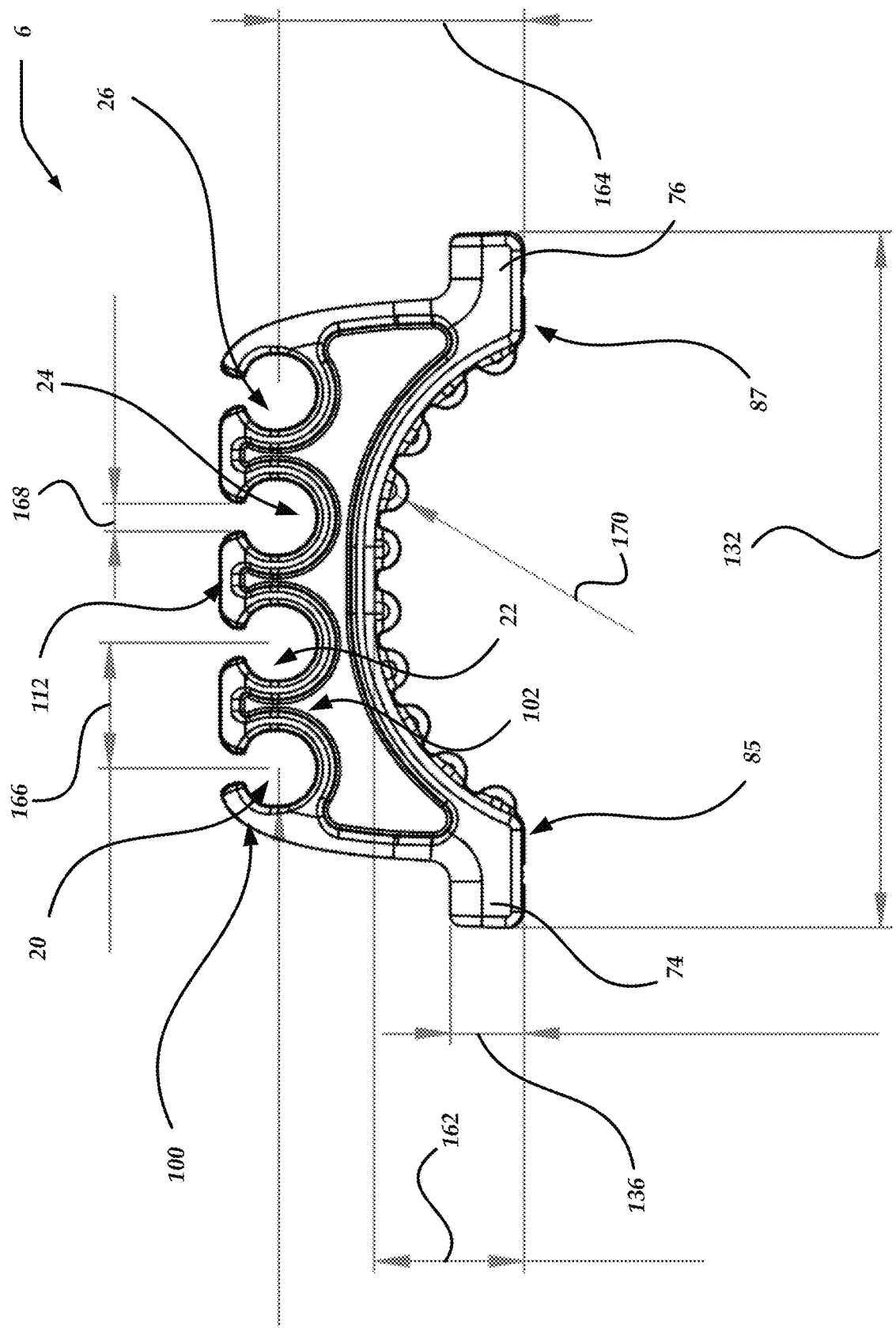
FIG. 17 is an isometric side elevational view of the secure line holder of FIG. 15.

Each receptacle preferably has one or more holder fasteners, such as holder snaps 50 and 52 (see FIG. 5), that separably secure a respective one of the secure line holders 6-10 to the tray 4. The distance between holder fasteners of a given receptacle, such as distance 130 (see FIG. 10), preferably approximates the length of the corresponding one of the secure line holders 6-10, such as the length 132 of the secure line holder 6 (see FIG. 17). The tray 4 preferably has sidewalls 70 and 72 that extend along the length of the tray 4 opposite the longitudinal axis 18 of the tray 4 from each other (see FIG. 7). The sidewalls 70 and 72 preferably have high regions, such as high regions 74-80, and low regions, such as low regions 82-86, that are sequentially distributed between the high regions along the lengths of the sidewalls 70 and 72. The high regions of the sidewall 70 are preferably longitudinally aligned with the high regions of the sidewall 72, and the low regions of the sidewall 70 are preferably longitudinally aligned with the low regions of the sidewall 72. One holder fastener of a given one of the receptacles 12-16 is preferably disposed between an opposing pair of high regions, and another holder fastener of the given one of the receptacles 12-16 is preferably disposed between another opposing pair of high regions, and the high regions preferably each extend from one receptacle to the next, thereby increasing the rigidity of the tray 4 along those regions to increase the reliability of the securing of the secure line holders 6-10 to the tray 4. The low regions being sequentially distributed between the high regions facilitates increasing the overall flexibility of the tray 4, thereby increasing the ease with which medical personnel may peel the tray 4 off the surgery bed surface.

Figure 5:
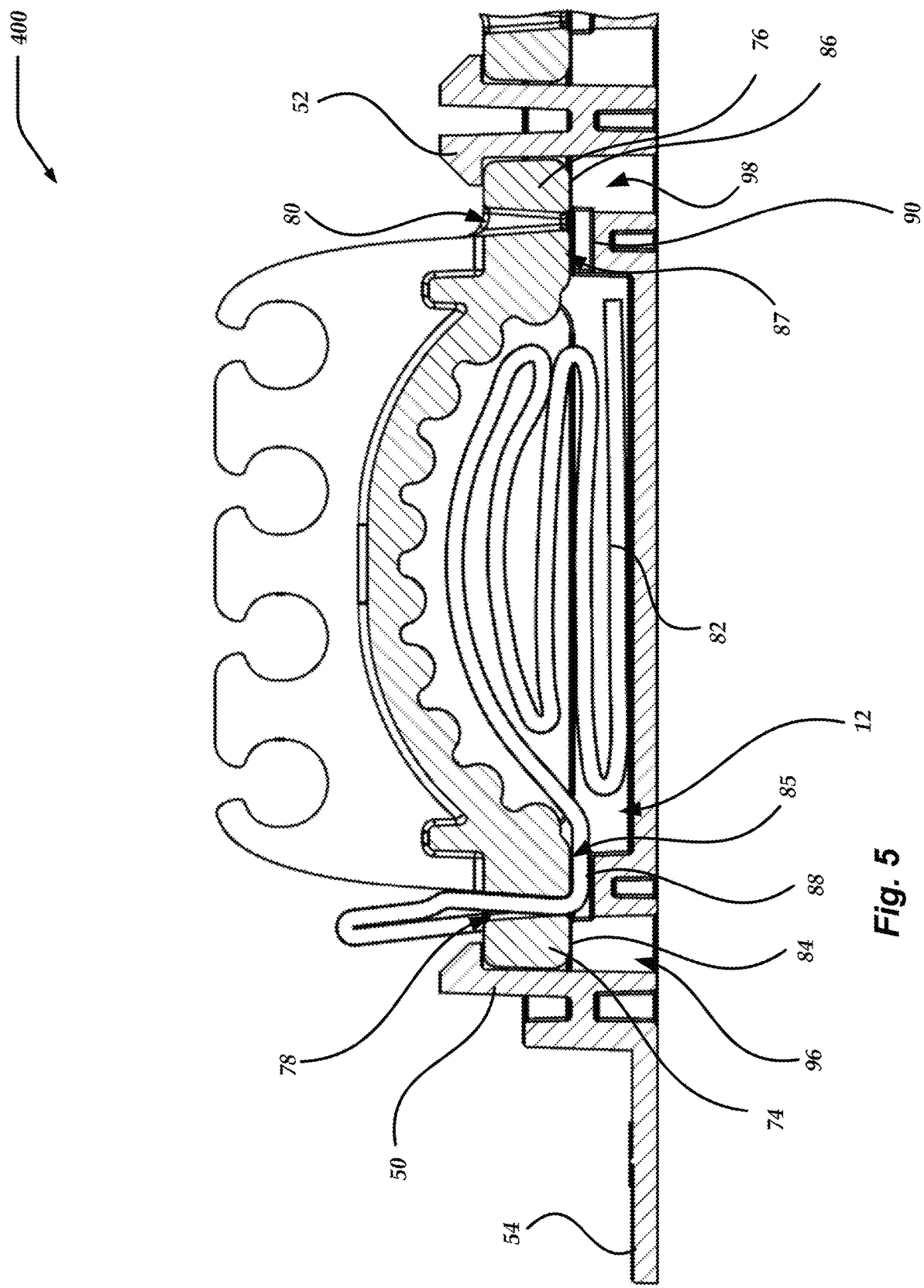
FIG. 5 is a cross-sectional view of a portion of the secure line holder system of FIG. 1, including a stored coupler.
Figure 16:
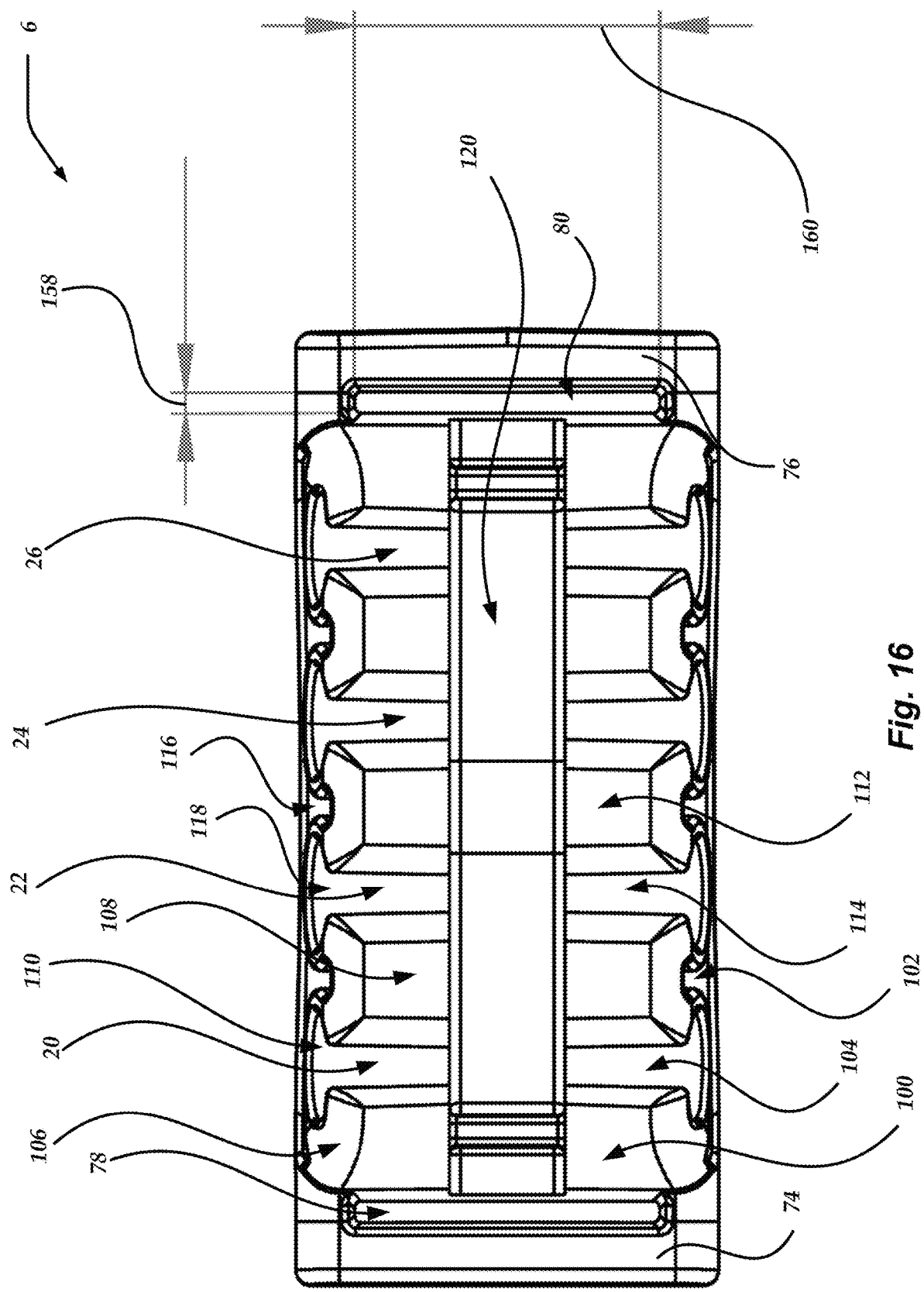
FIG. 16 is an isometric overhead view of the secure line holder of FIG. 15.
Figure 18:
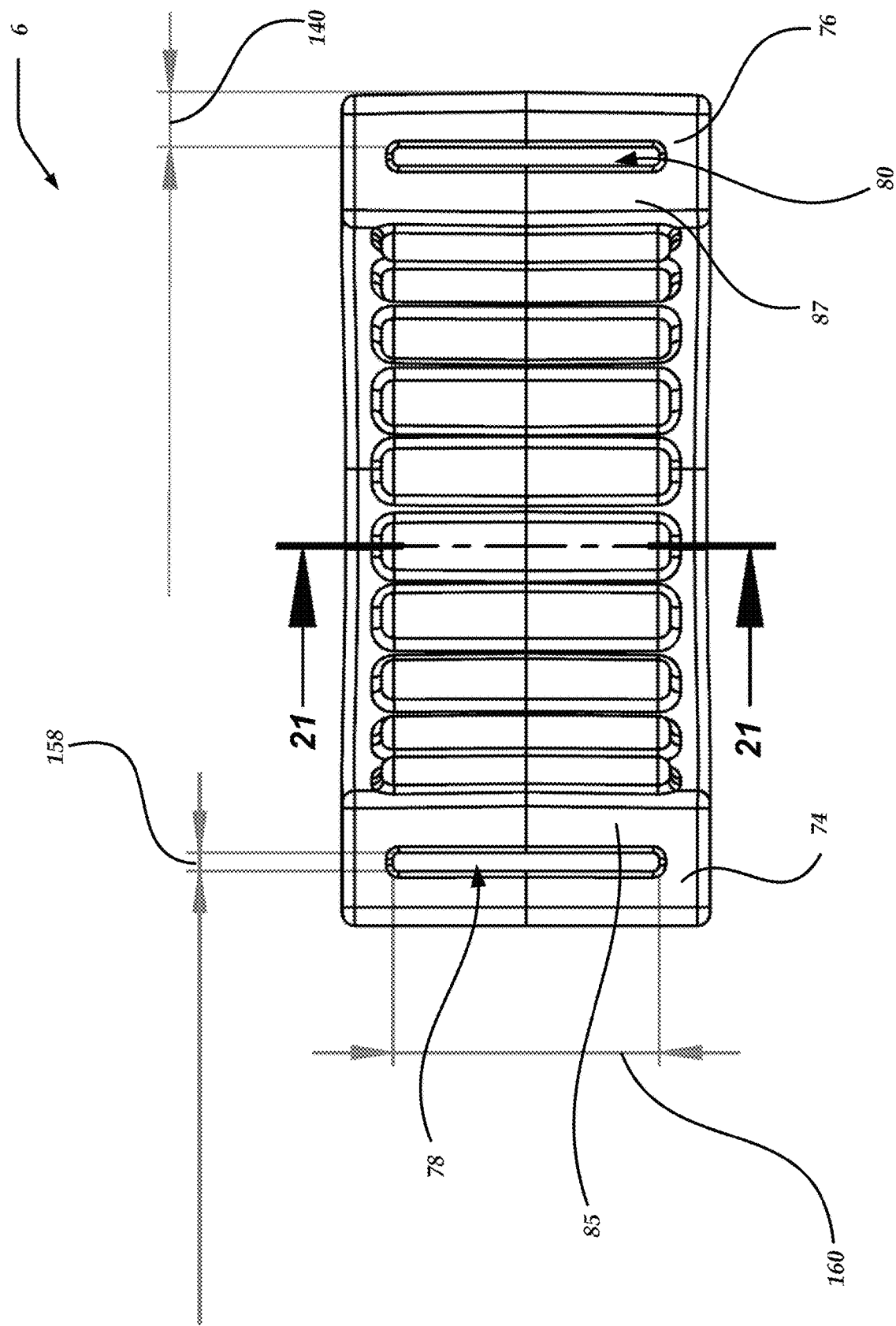
FIG. 18 is an isometric underside view of the secure line holder of FIG. 15.

The secure line holders 6-10 preferably each have flanges, such as flanges 74 and 76 (see FIG. 17), that facilitate the holder fasteners securing the secure line holders 6-10 to the tray 4 (see FIG. 5). The flanges preferably each define a rail coupler slot such as a strap slot, for example strap slots 78 and 80 (see FIGS. 16 and 18), that is configured to receive a rail coupler such as a strap, for example strap 83 (see FIGS. 4 and 5), to facilitate securing the secure line holders 6-10 to the bed rail. The bottom surface of each of the secure line holders 6-10 preferably has an arcuate shape between the flanges (see FIGS. 5 and 17) to facilitate securing the secure line holders 6-10 to the bed rail. The bottom surface of each of the secure line holders 6-10 preferably has flat regions, such as flat regions 85 and 87 (see FIGS. 5 and 17), disposed between the arcuate shaped region and the flanges to increase the surface area in contact with the tray 4 when the secure line holders 6-10 are secured therein.

Figure 8:
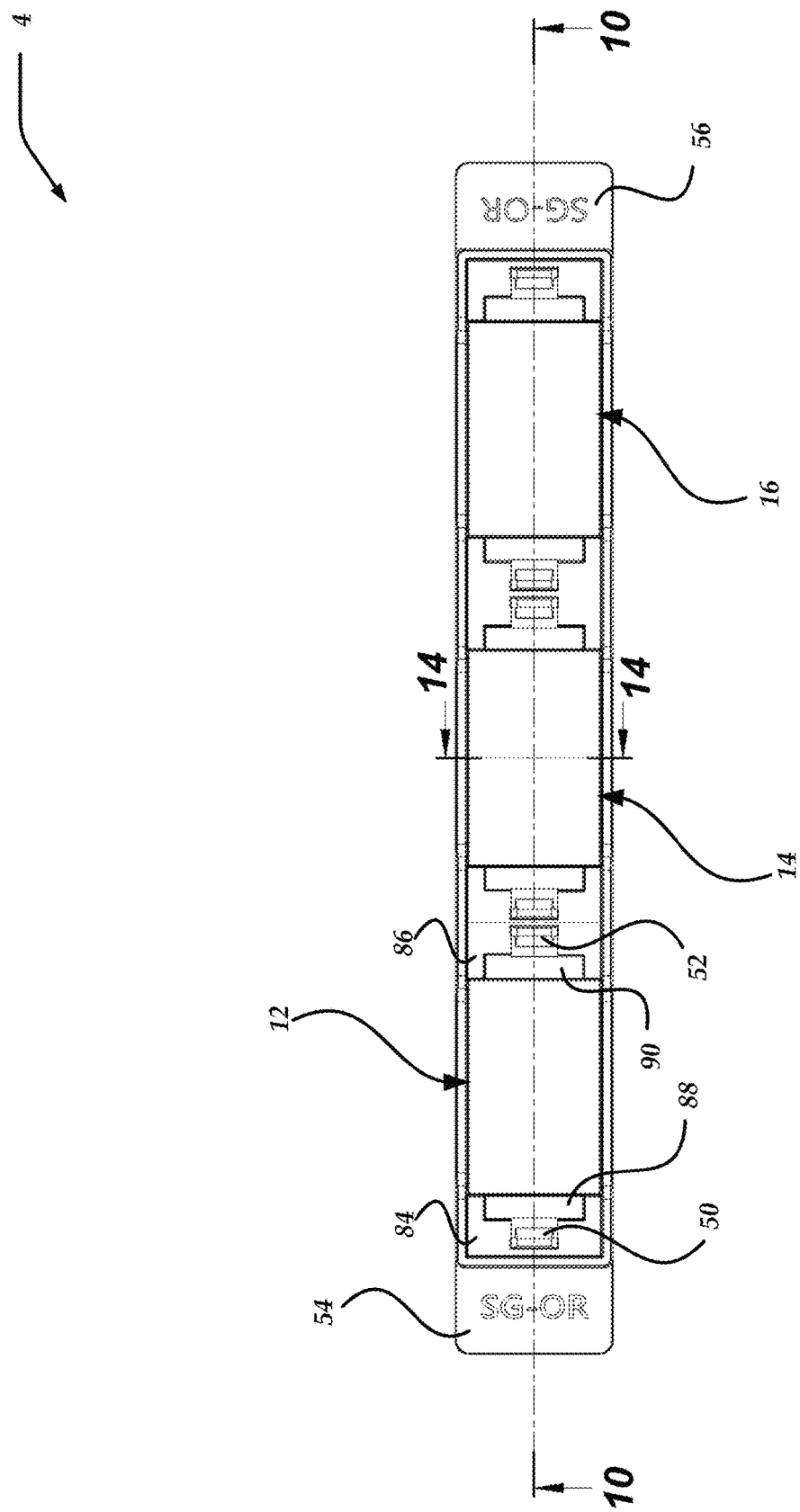
FIG. 8 is an isometric overhead view of the tray of FIG. 1.
Figure 9:
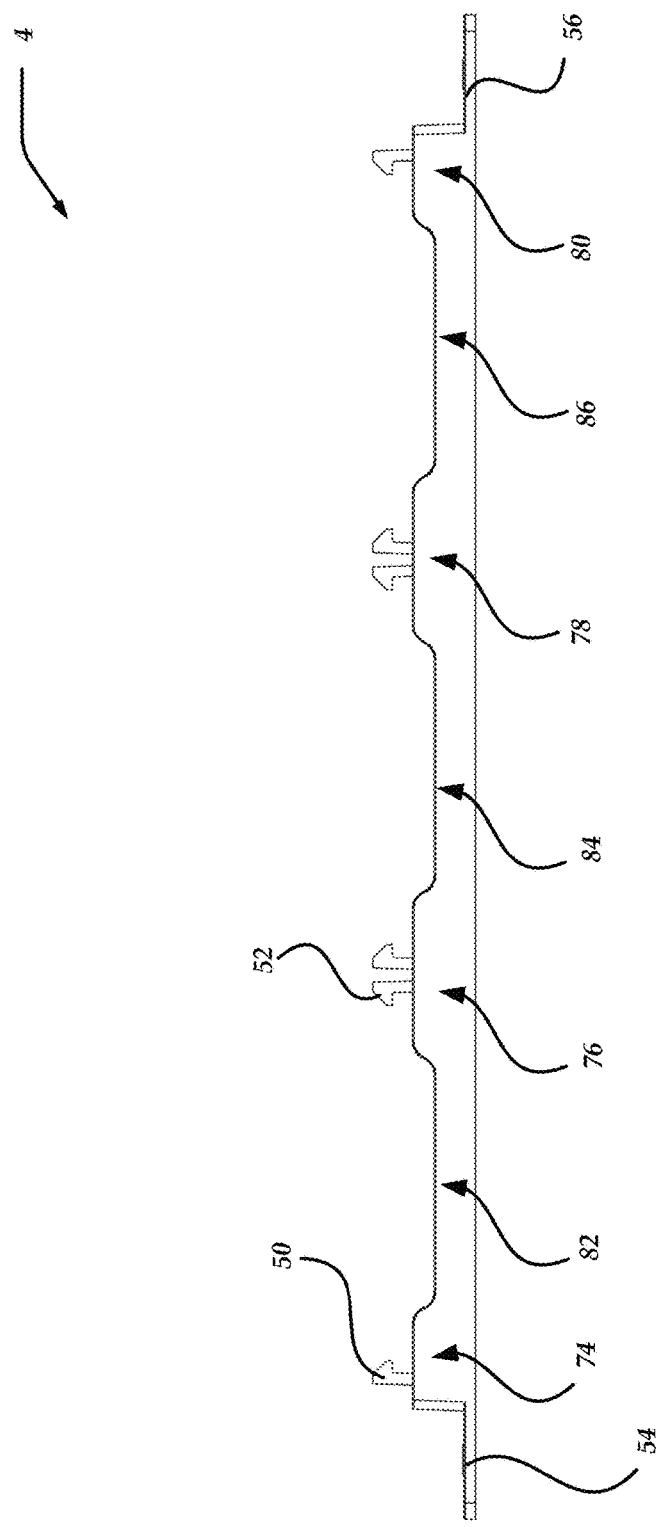
FIG. 9 is an isometric side elevational view of the tray of FIG. 1.
Figure 11:
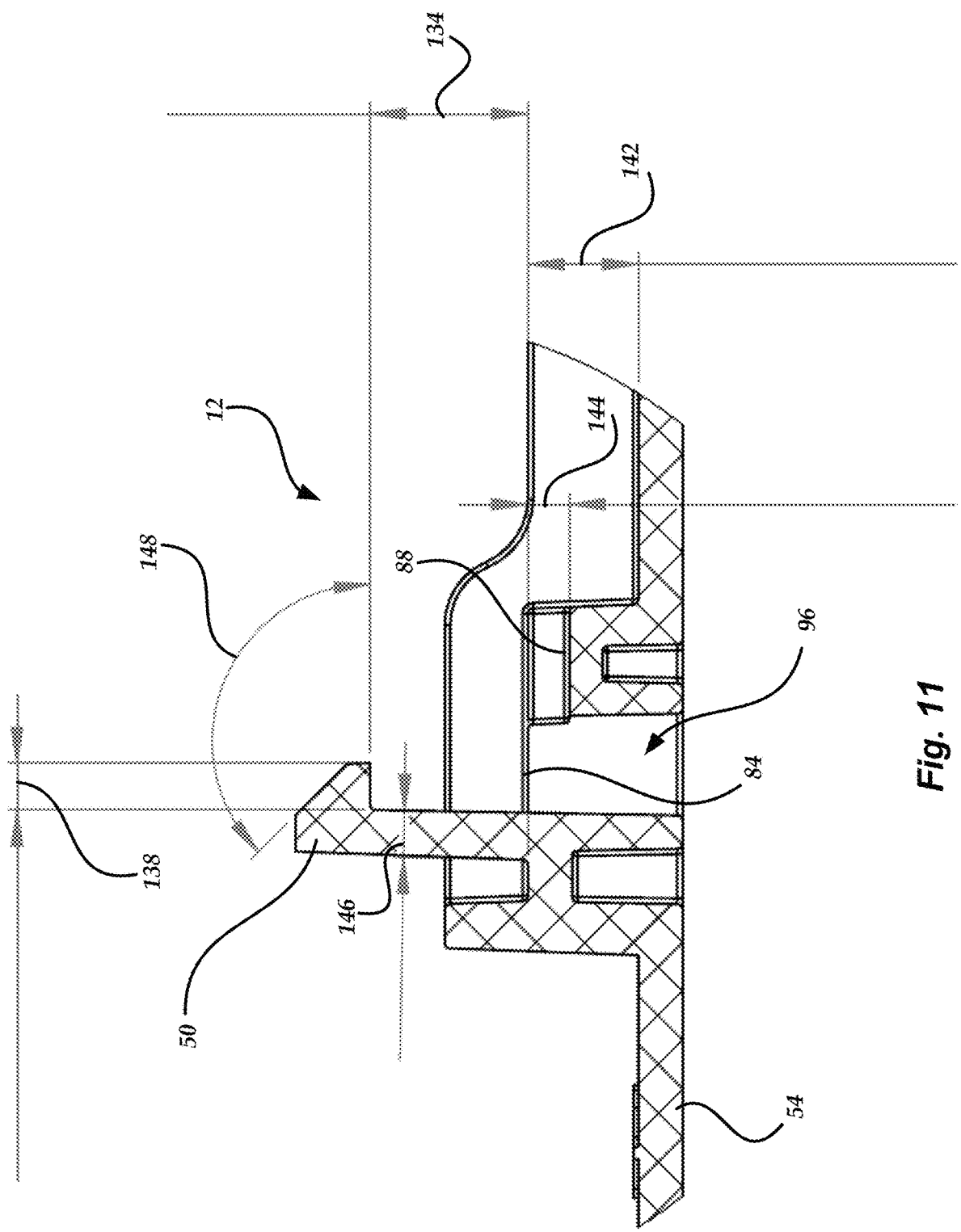
FIG. 11 is an isometric cross-sectional view of a portion of the tray of FIG. 1.

Each longitudinal end portion of each receptacle in the tray 4 preferably has an elevated portion, such as elevated portions 88 and 90, and a recessed portion, such as recessed portions 92 and 94 (see FIGS. 5 and 8). The elevated portions are preferably configured to support one or more of the flanges or the flat regions of the bottom surfaces of the secure line holders 6-10 when the secure line holders 6-10 are secured in the tray 4. Accordingly, the distance between the upper surface of each of the elevated portions and the bottom lip of the corresponding holder fastener, such as the distance 134 (see FIG. 11), preferably approximates the height of the corresponding flange of the corresponding secure line holder, such as the height 136 (see FIG. 17). The elevated portions are preferably U-shape, and the recessed portions are preferably arranged to align with the corresponding slots of the secure line holders 6-10 when the secure line holders 6-10 are secured in the tray 4. The recessed portions are preferably configured to receive the straps to facilitate the straps extending through corresponding slots in the corresponding secure line holders while having the remainder of the straps stored in the corresponding receptacles under the arcuate portions of the bottoms of the secure line holders (see FIG. 5). Accordingly, the length of the lip of each of the holder fasteners, such as the length 138 (see FIG. 11), is preferably equal to or less than the length of the corresponding flange of the corresponding secure line holder, such as the length 140 (see FIG. 18). Also accordingly, the height of each of the elevated portions, such as the height 142 (see FIG. 11), is preferably greater than the height of the corresponding recess portion by an amount that matches or exceeds the thickness of the corresponding strap, such as the amount 144 (see FIG. 11). The tray 4 preferably defines a gap, such as gaps 96 and 98, between the holder fasteners and the corresponding recessed portions (see FIGS. 5,6, and 12) to facilitate movement of the holder fasteners.

Figure 15:
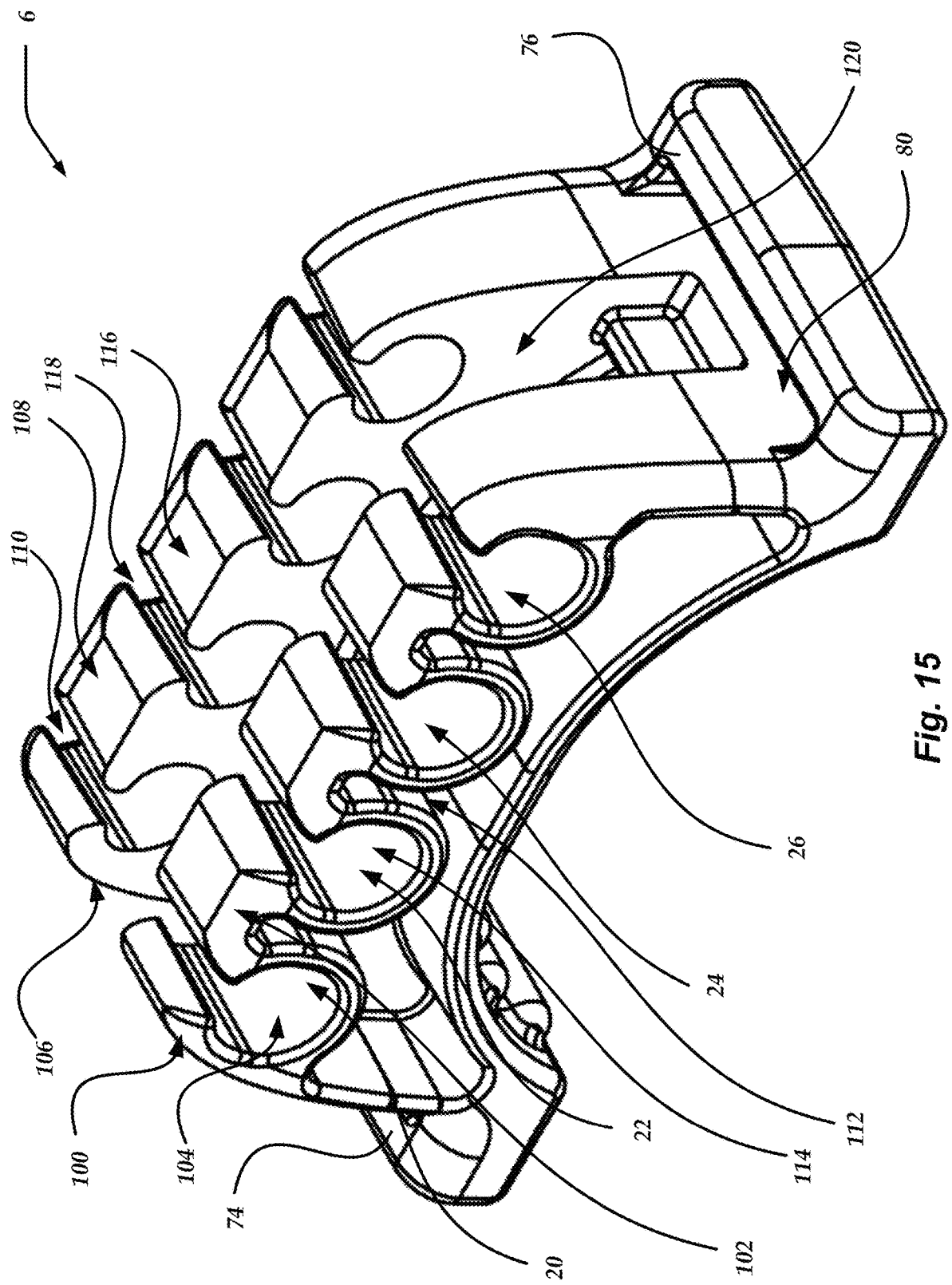
FIG. 15 is a perspective isometric view of the separated secure line holder of FIG. 2.

As shown in FIG. 15, each line channel in the secure line holders 6-10 is preferably defined by one or more pairs of channel walls. For example, the line channel 20 is preferably defined by channel walls 100 and 102 that define a channel portion 104 and also by channel walls 106 and 108 that define a channel portion 110. As another example, the line channel 22 is preferably defined by channel walls 102 and 112 that define a channel portion 114 and also by channel walls 108 and 116 that define a channel portion 118. Accordingly, each channel preferably includes two channel portions that are spaced apart from each other by a finger channel 120 that is also defined by the channel walls that define the channels. The finger channel 120 is preferably configured to facilitate medical personnel inserting a finger in the finger channel 120 and under one or more lines held in the secure line holder 6 to pull the one or more lines out of and away from the secure line holder 6. The finger channel 120 also facilitates medical personnel visually inspecting the portion of each line held in the secure line holder 6 that is disposed between the two channel portions that form the corresponding line channel.

Figure 14:
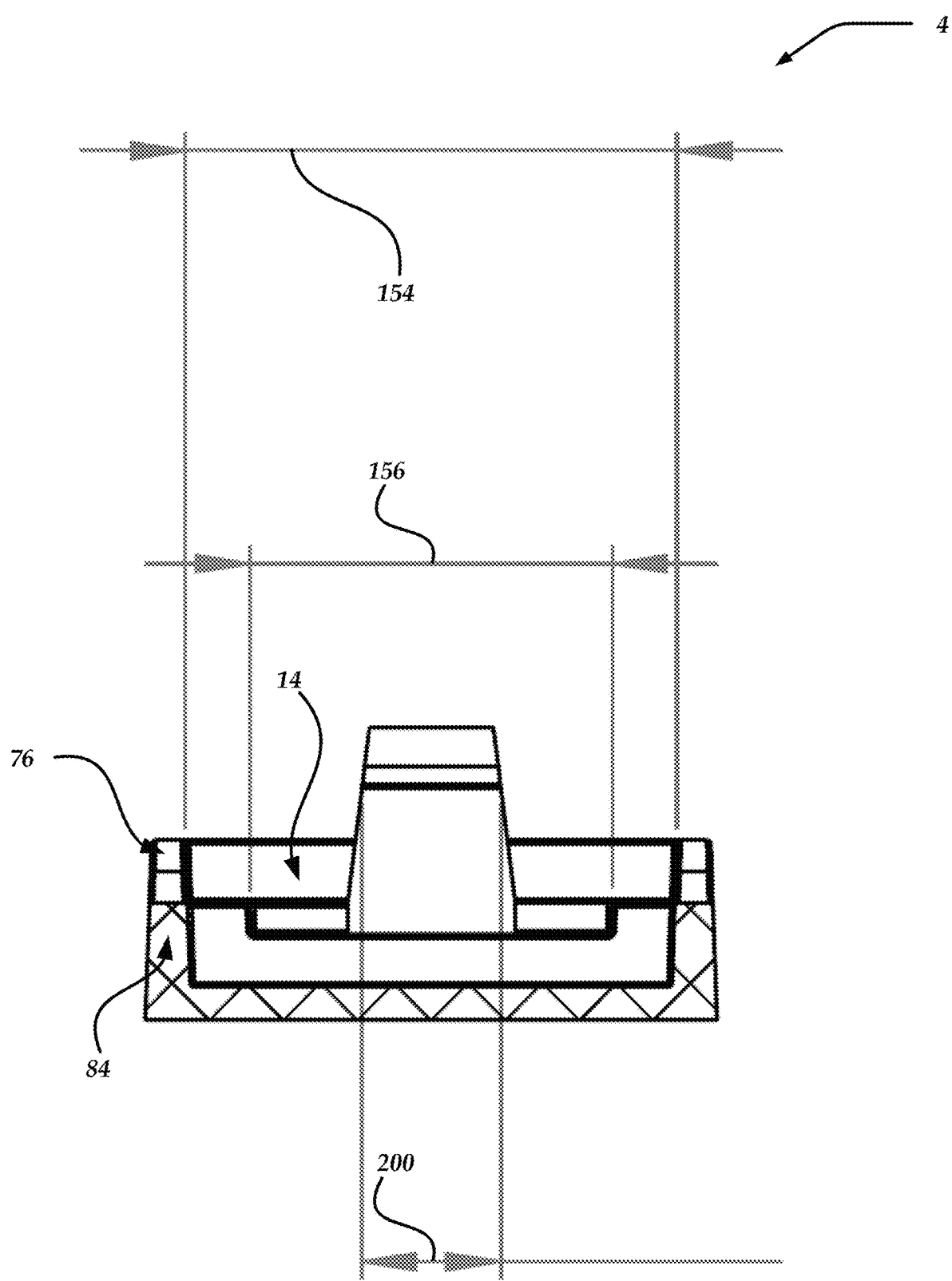
FIG. 14 is an isometric cross-sectional view of the tray of FIG. 1, taken along line 14-14 in FIG. 8.

The holder fasteners preferably have a thickness, such as the thickness 146 (see FIG. 11), of 2.15 mm. Each lip of each holder fastener preferably has a width, such as width 200 (see FIG. 14), of 8.44 mm. The tops of the holder fasteners preferably have a chamfer that facilitates guiding the secure line holders into the receptacles. The chamfers preferably have an angle, such as the angle 148 (see FIG. 11), of 135 degrees. The tray 4 preferably has a length 150 (see FIG. 12) of 263.91 mm. The tray 4 preferably has a width 152 (see FIG. 12) of 34.67 mm and, most preferably, exceeds the width of the widest secure line holder. Each receptacle preferably has a width, such as width 154 (see FIG. 14), of 29.83 mm and, most preferably, that matches or exceeds the width of the corresponding secure line holder. Each recessed portion of each receptacle preferably has a width, such as width 156 (see FIG. 14), of 21.95 mm and, most preferably, matches or exceeds the width of the corresponding strap. Each lip of each holder fastener preferably has a length, such as length 138 (see FIG. 11), of 2.17 mm.

Each slot preferably has a width, such as width 160 (see FIG. 16), of 21.23 mm and, most preferably, matches or exceeds the width of the corresponding strap. Each slot preferably has preferably has a length, such as length 158 (see FIG. 16), of 1.45 mm and, most preferably, matches or exceeds the thickness of the corresponding strap. The arcuate shape of the middle portion of the bottom of each secure line holder preferably has a height relative to the flat bottom regions of the secure line holder, such as height 162 (see FIG. 17), of 14.25 mm. The arcuate shape of the middle portion of the bottom of each secure line holder preferably has a radius, such as radius 170 (see FIG. 17), of 19 mm and, most preferably, approximates the radius of the bed rail or other apparatus to which the secure line holder is expected to be secured. The center of each line channel is preferably arranged at a height relative to the flat bottom regions of the secure line holder, such as height 164 (see FIG. 17), of 23.41 mm to facilitate increasing ease at which the medical personnel can insert or remove lines while the secure line holder is secured to the tray 4 or a bed rail. The centers of sequentially adjacent line channels are preferably spaced apart from each other by a distance, such as distance 166 (see FIG. 17), of 12 mm to facilitate increasing ease at which the medical personnel can insert or remove lines from a given line channel while a line is secured in a sequentially adjacent line channel. That channel walls in each pair of channel walls that define a channel portion of each line channel are preferably spaced apart from each other by a distance, such as distance 168 (see FIG. 17), of 2.64 mm to facilitate increasing the ease at which the medical personnel can insert or remove lines from the line channel while sufficiently securing the lines in the line channel.

Figure 19:
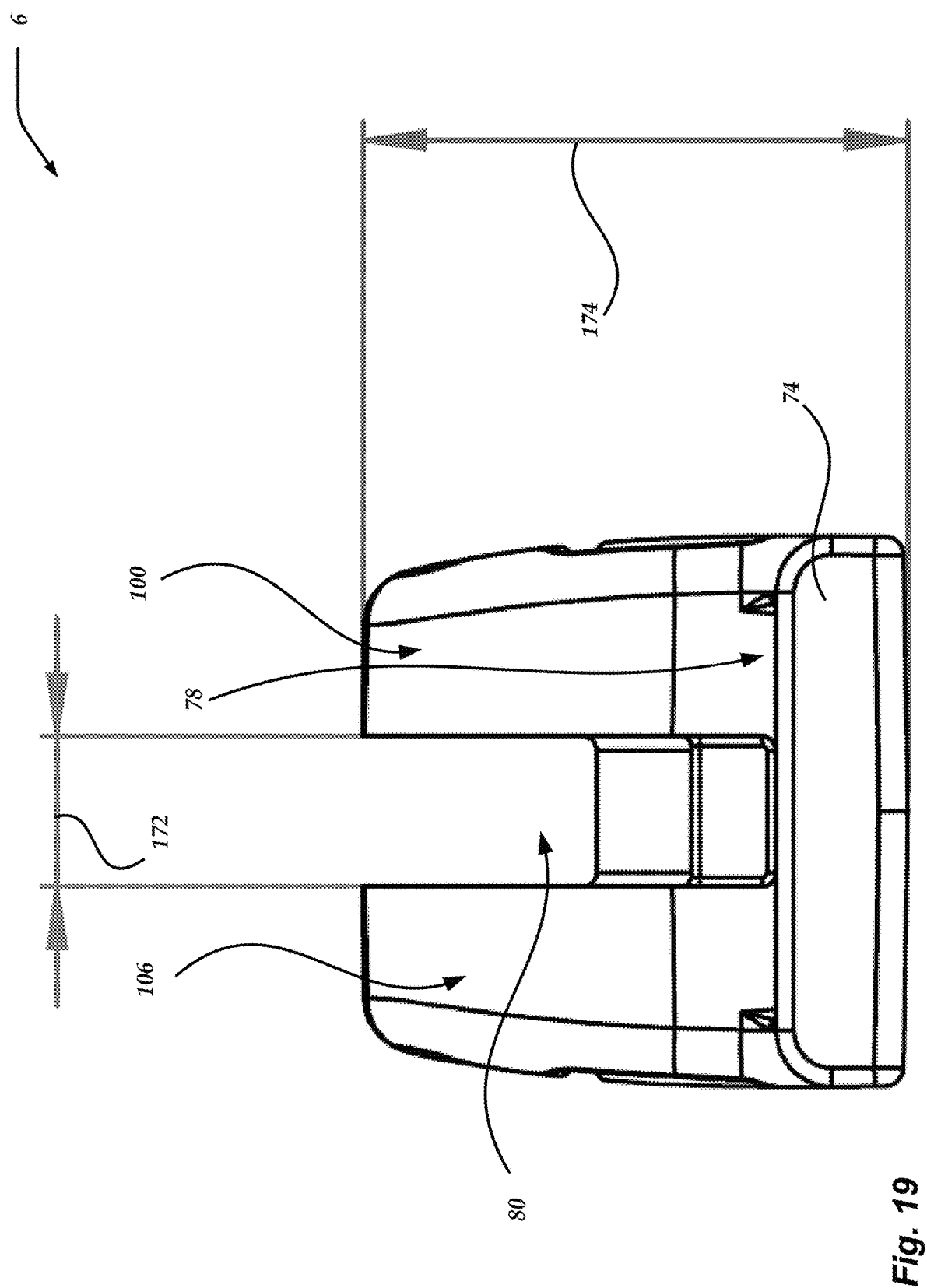
FIG. 19 is an isometric side elevational view of the secure line holder of FIG. 15.
Figure 20:
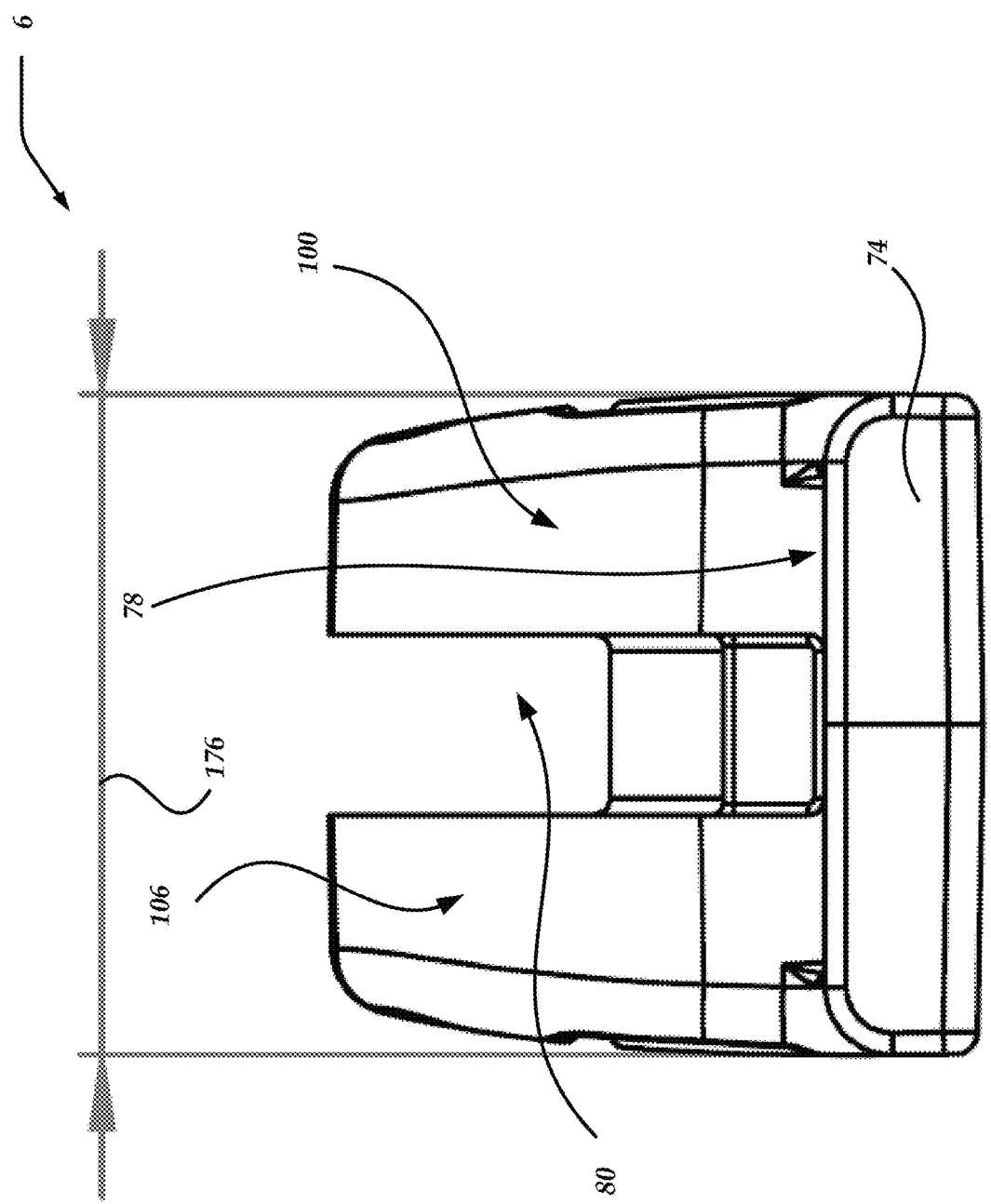
FIG. 20 is an isometric side elevational view of the secure line holder of FIG. 15.
Figure 21:
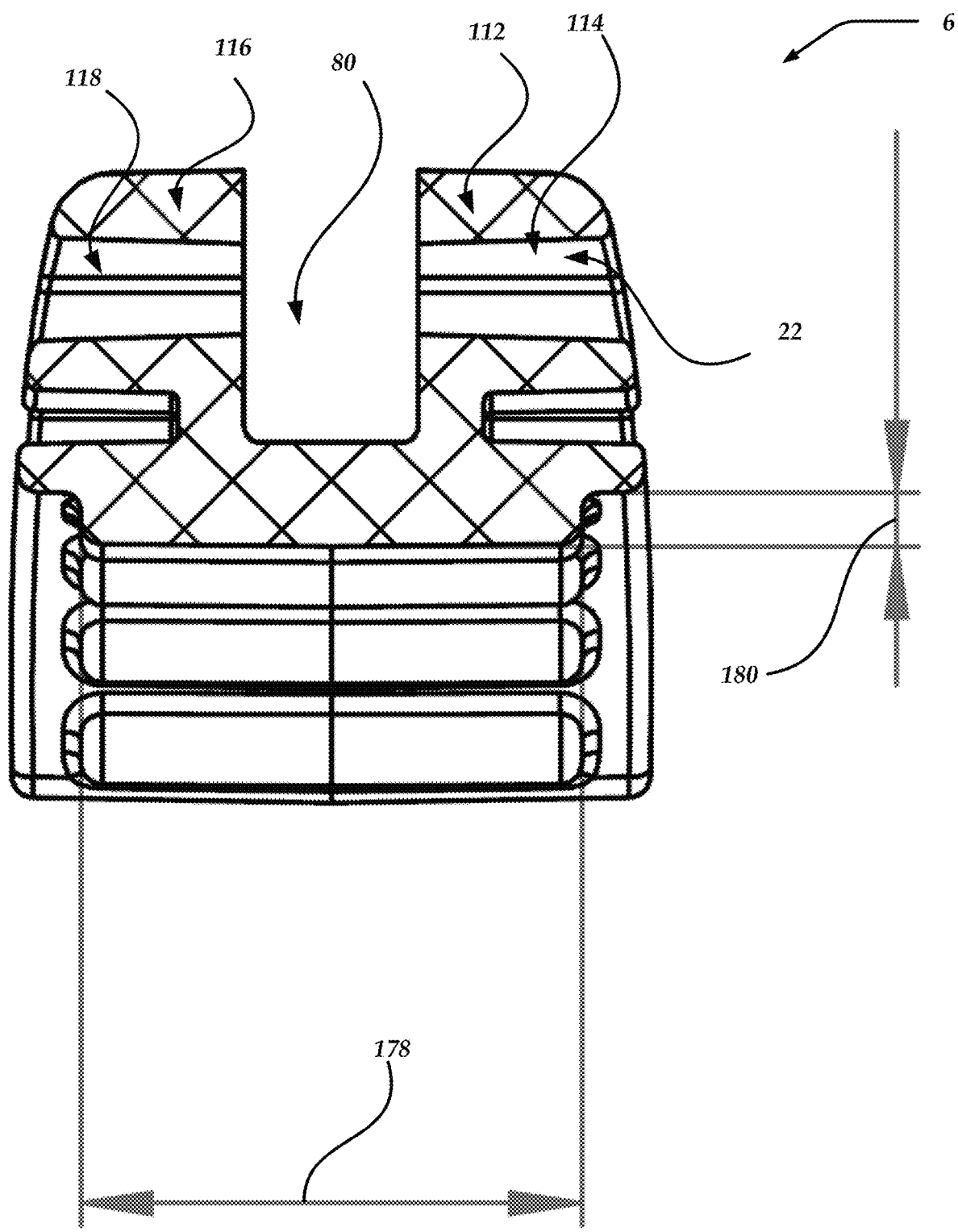
FIG. 21 is an isometric cross-sectional view of the secure line holder of FIG. 15, taken along line 21-21 of FIG. 18.

The finger channel of each secure line holder preferably has a width, such as width 172 (see FIG. 19), of 8 mm to facilitate increasing the ease at which the medical personnel can insert or remove lines from the line channels of the secure line holder. Each secure line holder preferably has a height, such as height 174 (see FIG. 19), of 29 mm. Each secure line holder preferably has a width, such as width 176 (see FIG. 20), of 29.35 mm. Each bump in the arcuate shaped middle portion of the bottom of each secure line holder preferably has a width, such as width 178 (see FIG. 21), of 23 mm. Each bump in the arcuate shaped middle portion of the bottom of each secure line holder preferably has a length, such as length 180 (see FIG. 21), of 2.45 mm. The tray 4 and the secure line holders are preferably made from one or more polymers, such as thermoset or thermoplastic polymers, such as acrylonitrile butadiene styrene (ABS).

Each dimension or angle described herein is intended to disclose multiple ranges of dimensions or angles, such as a range extending from the dimension or angle to 10, 20, 30, 40, 50, 75, 100, or more percent greater than the range or angle, a range extending from the dimension or angle down to 10, 20, 30, 40, 50, 75, or more percent less than the dimension or angle, or a range extending between those upper and lower extremes as defined by those percentages of the dimension or angle. Any one or more features disclosed in U.S. Provisional Application No. 62/826,624 may be implemented with the secure line holder disclosed herein, in combination with or instead of one or more corresponding features disclosed herein. Any dimension from that provisional application may be implemented with any corresponding feature disclosed herein.

As used herein, the following terms take the meanings explicitly associated herein, unless the context clearly dictates otherwise. The term "or" is an inclusive grammatical conjunction to indicate that one or more of the connected terms may be employed. For example, the phrase "one or more A, B, or C" or the phrase "one or more As, Bs, or Cs" is employed to discretely disclose each of the following: i) one or more As, ii) one or more Bs, iii) one or more Cs, iv) one or more As and one or more Bs, v) one or more As and one or more Cs, vi) one or more Bs and one or more Cs, and vii) one or more As, one or more Bs, and one or more Cs. The articles "a," "an," and "the" include plural references. Plural references are intended to also disclose the singular.

The terms "height," "length," "width," and "thickness" are defined relative to the longitudinal axis of the tray 4 when the secure line holders are secured to the tray 4. The length of a given element corresponds to the dimension of the element as measured parallel to the longitudinal axis of the tray 4. The width of a given element is measured parallel to the bottom surface of the tray 4 and transverse (for example, perpendicular) to the longitudinal axis of the tray 4. The height of a given element is measured transverse (for example, perpendicular) to both the length and the width. The term "transverse" refers to a non-parallel orientation and includes yet is not limited to a perpendicular orientation. The terms "configured", "arranged", or derivatives thereof refer to one or more of sized, dimensioned, positioned, or oriented. The term "approximates" or derivatives thereof refers to equal to or within 10, 20, 30, 40, 50, 75, or 100 percent.

While the preferred embodiment of the invention has been illustrated and described, as noted above, many changes can be made without departing from the spirit and scope of the invention. For example, each disclosure of a component preferably having a feature or characteristic is intended to also disclose the component as being devoid of that feature or characteristic, unless the principles of the invention clearly dictate otherwise. Accordingly, the scope of the invention is not limited by the disclosure of the preferred embodiment. Instead, the invention should be determined entirely by reference to the claims that follow. It should also be noted that the claim dependencies or combinations of elements recited in the claims does not reflect an intention to forgo claiming other subject matter disclosed herein. Instead, it should be reasonably expected that the applicant intends to eventually prepare claims directed toward each and every feature or characteristic disclosed herein. Moreover, this disclosure is intended to disclose the subject matter of any combination of any two or more of the claims, such that subsequent claim sets may recite that any one of the dependent claims depends from any other one or more claims, up to and including all other claims in the alternative (for example, "The system of any one of the preceding or subsequent claims . . . ."). This disclosure is also intended to disclose the subject matter of any one of the dependent claims, as if it was an independent claim, with or without all or a portion of the subject matter of the original independent claim(s) or any other subject matter disclosed herein.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

I claim:

1. A medical line holder system comprising:
   a tray having a holder receptacle, the tray being configured to couple to a head of a surgery bed; and
   a secure line holder, the holder receptacle being configured to receive and separably secure the secure line holder, the secure line holder being configured to securely hold multiple medical lines both while being secured in the holder receptacle and while being separated from the tray, the secure line holder being configured to separably couple to a bed rail of a hospital transportation bed or a hospital recovery bed after being separated from the tray,
   wherein the tray has a longitudinal axis, the secure line holder defining a finger channel that extends along the longitudinal axis of the tray while the secure line holder is secured in the receptacle, the finger channel being configured to receive an instrument between the secure line holder and a held line to facilitate removal of the line from the secure line holder.

2. The medical line holder system of claim 1, wherein the tray has a longitudinal axis, the secure line holder defining a plurality of line channels that are each configured to securely hold a respective one of the multiple medical lines, the secure line holder having a first coupler and a second coupler disposed opposite the line channels from the first coupler, the first and second couplers of the secure line holder being configured to separably couple to the tray.

3. The medical line holder system of claim 1, wherein the tray has a longitudinal axis, the secure line holder being disposed along the longitudinal axis of the tray while being secured in the receptacle, the secure line holder being configured to orient the held medical lines with longitudinal axes of the held medical lines oriented transverse to the longitudinal axis of the tray while the secure line holder is secured in the receptacle and parallel to the bed rail while the secure line holder is coupled to the bed rail.

4. The medical line holder system of claim 1, wherein the receptacle of the tray has an elevated portion and a recessed portion, the secure line holder having a rail coupler that couples the secure line holder to the bed rail, the elevated portion supporting the secure line coupler and the recessed portion of the receptacle aligning with the rail coupler while the secure line holder is secured to the tray to facilitate storing the rail coupler between the secure line holder and the tray.

5. The medical line holder system of claim 1, wherein the tray defines a longitudinal axis and has a sidewall that extends along the longitudinal axis of the tray, the sidewall having a high region and a low region sequentially distributed along the sidewall.

6. The medical line holder system of claim 1, wherein the tray has a holder fastener and a sidewall that extends along the longitudinal axis of the tray, the sidewall having a high region and a low region sequentially distributed along the sidewall, the high region aligning with the fastener relative to a position of the fastener along the longitudinal axis of the tray.

7. The medical line holder system of claim 1, wherein the tray has a flange that extends away from the receptacle along the longitudinal axis of the tray.

8. A method of securing medical lines, the method comprising:
   providing a medical line holder system that includes:
      a tray having a holder receptacle, the tray being configured to couple to a head of a surgery bed; and
      a secure line holder, the holder receptacle being configured to receive and separably secure the secure line holder, the secure line holder being configured to securely hold multiple medical lines both while being secured in the holder receptacle and while being separated from the tray, the secure line holder being configured to separably couple to a bed rail of a hospital transportation bed or a hospital recovery bed after being separated from the tray;
   coupling the tray to the head of the surgery bed;
   securing the multiple medical lines to the secure line holder;
   after surgery of a patient, separating the secure line holder from the tray; and
   coupling the secure line holder to the bed rail of the hospital transportation bed or the hospital recovery bed.

9. The method of claim 8, wherein securing the multiple medical lines to the secure line holder includes securing the multiple medical lines to the secure line holder while the secure line holder is coupled to the tray.

10. The method of claim 8, wherein separating the secure line holder from the tray includes separating the secure line holder from the tray without removing the multiple medical lines from the secure line holder.

11. The medical line holder system of claim 1, wherein the surgery bed includes a mattress or table on which a patient lies during surgery, and the tray is configured to couple to a flat surface of the mattress or table.

12. The method of claim 8, wherein the surgery bed includes a mattress or table on which the patient lies during surgery, and coupling the tray to the head of the surgery bed includes coupling the tray to a flat surface of the mattress or table.

* * * * *